United States Patent
Goto

(10) Patent No.: US 10,517,534 B2
(45) Date of Patent: Dec. 31, 2019

(54) BLOOD VESSEL DETECTION APPARATUS, MAGNETIC RESONANCE IMAGING APPARATUS AND PROGRAM

(71) Applicant: General Electric Company, Schenectady, NY (US)

(72) Inventor: Takao Goto, Tokyo (JP)

(73) Assignee: General Electric Company, Schenectady, NY (US)

( * ) Notice: Subject to any disclaimer, the term of this patent is extended or adjusted under 35 U.S.C. 154(b) by 119 days.

(21) Appl. No.: 15/847,271

(22) Filed: Dec. 19, 2017

(65) Prior Publication Data
US 2018/0177452 A1 Jun. 28, 2018

(30) Foreign Application Priority Data
Dec. 27, 2016 (JP) .................. 2016-253456

(51) Int. Cl.
| | | |
|---|---|---|
| *A61B 5/00* | (2006.01) | |
| *A61B 5/055* | (2006.01) | |
| *G01R 33/56* | (2006.01) | |
| *G01R 33/54* | (2006.01) | |
| *G01R 33/563* | (2006.01) | |
| *G06T 7/73* | (2017.01) | |

(52) U.S. Cl.
CPC .............. *A61B 5/489* (2013.01); *A61B 5/055* (2013.01); *A61B 5/7264* (2013.01); *G01R 33/543* (2013.01); *G01R 33/5607* (2013.01); *G01R 33/5608* (2013.01); *G01R 33/5635* (2013.01); *G06T 7/73* (2017.01); *A61B 2576/02* (2013.01); *G06T 2207/10088* (2013.01); *G06T 2207/30048* (2013.01); *G06T 2207/30101* (2013.01)

(58) Field of Classification Search
CPC ....... A61B 5/489; A61B 5/055; A61B 5/7264; G01R 33/5607; G01R 33/543; G01R 33/5608; G01R 33/5635; G06T 7/73
See application file for complete search history.

(56) References Cited

U.S. PATENT DOCUMENTS

| | | | |
|---|---|---|---|
| 6,178,220 B1 * | 1/2001 | Freundlich ............ | G06T 11/003 378/15 |
| 7,821,267 B2 * | 10/2010 | Yatsui .................. | A61B 5/0555 324/318 |
| 2018/0357796 A1 * | 12/2018 | Bishop ................... | G06T 7/55 |

* cited by examiner

*Primary Examiner* — Dixomara Vargas

(57) ABSTRACT

An MRI apparatus comprises a image producing unit 101 for producing an image of a first body part containing a blood vessel; a defining unit 108 for defining a slice intersecting the image based on a reference position Q within the first body part, the slice being defined so that an angle of the slice is changeable with respect to the blood vessel VE; a unit for obtaining an index VI for deciding whether or not the blood vessel VE is contained within the slice for each angle θ; and a determining unit 111 for determining an angle of the slice at which the blood vessel VE is contained in the slice based on the index VI.

12 Claims, 22 Drawing Sheets

| Localizer scan LS | 3D data acquisition scan AS | Main scan MS |

FIG. 3

Cross-sectional image DV in vertical plane VS

Cross-sectional image DO in oblique plane OB

US 10,517,534 B2

BLOOD VESSEL DETECTION APPARATUS, MAGNETIC RESONANCE IMAGING APPARATUS AND PROGRAM

CROSS-REFERENCE TO RELATED APPLICATION

This application claims priority to Japanese Patent Application No. 2016-253456, filed on Dec. 27, 2016, the entirety of which is incorporated herein by reference.

BACKGROUND

The present invention relates to a blood vessel detection apparatus for detecting a blood vessel, a magnetic resonance imaging apparatus for acquiring an image of a subject and detecting a blood vessel from the acquired image, and a program for detecting a blood vessel.

A magnetic resonance imaging apparatus for imaging a subject using a contrast medium is known. Methods of imaging a subject using a contrast medium include, as an example, a method in which an operator manually defines a slice (for example, an axial slice) intersecting an aorta, a cross-sectional image in the slice is displayed on a display screen in real time, and the operator checks whether or not a bolus of the contrast medium has flown into the aorta while observing the cross-sectional image displayed on the display screen. In this method, once the operator has decided that a bolus of the contrast medium has reached the aorta, an imaging sequence for acquiring an image of a body part to be imaged is performed. A contrast image of the imaged body part may thus be obtained.

The method, however, poses a problem that the operator's workload becomes higher because the operator has to manually define a slice intersecting the aorta. A technique of automatically detecting a position of the aorta is known. The method involves defining a plurality of axial planes in a body part containing a blood vessel to be detected, and detecting a position of a cross section of the aorta for each axial plane. Therefore, by using the prior art technique, it is possible to reduce the operator's workload.

As an example of the methods of imaging a subject using a contrast medium, there recently is a method of performing contrast imaging involving observing a bolus of the contrast medium at a position as close to the heart as possible. To enable observation of the bolus of the contrast medium at a position close to the heart, an operator manually defines a slice longitudinally cutting a blood vessel including the aortic arch in this method.

The blood vessel including the aortic arch, however, has a curved shape extending from the heart toward the back side, which is a complex shape. This poses a problem that it is difficult for the operator to manually define a slice. It may be contemplated to use the prior art detection technique in detecting a cross section of a blood vessel including the aortic arch. In the prior art method, however, an object to be detected is the aorta running along the backbone. The blood vessel including the aortic arch does not run along the backbone but does tortuously run from the heart toward the back side. This poses a problem, in that it is difficult to detect a blood vessel including the aortic arch by the prior art method.

Accordingly, it is desired to provide a technique capable of detecting a blood vessel that is difficult to detect in prior art techniques.

SUMMARY

In a first aspect, is a blood vessel detection apparatus comprises an image producing unit for producing an image of a first body part containing a blood vessel; a defining unit for defining a slice intersecting said image based on a reference position within the first body part, the slice being defined so that an angle of the slice is changeable with respect to the blood vessel; a unit for obtaining an index, the unit executing classification processing for classifying the blood vessel within the slice for each angle and obtaining an index representing a result of the classification; and a determining unit for determining an angle at which the slice contains the blood vessel based on the index.

In a second aspect, a magnetic resonance imaging apparatus comprises the blood vessel detection apparatus described regarding the first aspect.

In a third aspect, a program for causing a computer to execute image producing processing of producing an image of a first body part containing a blood vessel; defining processing of defining a slice intersecting the image based on a reference position within the first body part, the slice being defined so that an angle of the slice is changeable with respect to the blood vessel; processing of obtaining an index, the processing executing classification processing for classifying the blood vessel within the slice for each angle and obtaining an index representing a result of the classification; and determining processing of determining an angle at which the slice contains the blood vessel based on the index.

The angle of a slice is changed based on a reference position within the first body part. Then, classification processing for classifying the blood vessel within the slice is executed for each changed angle, and an index representing a result of the classification is obtained. The angle of a slice in which the blood vessel is contained may thus be determined.

BRIEF DESCRIPTION OF THE DRAWINGS

FIG. 3 is a diagram showing scans performed in the present embodiment;

DETAILED DESCRIPTION OF THE INVENTION

Now embodiments for practicing the invention will be described hereinbelow, although the present invention is not limited thereto.

Figure 1:
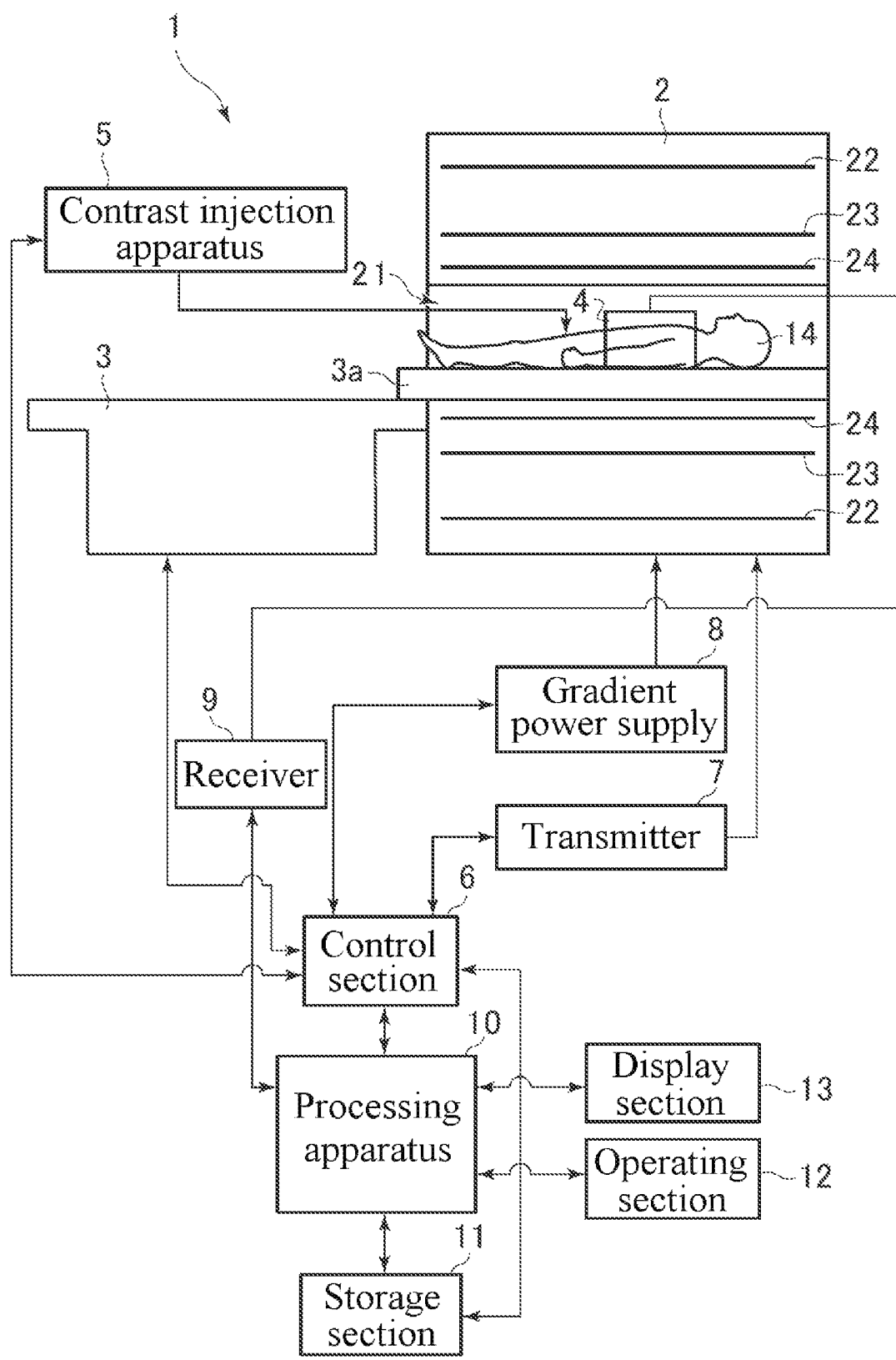
FIG. 1 is a schematic diagram of a magnetic resonance imaging (MRI) apparatus in one embodiment.

FIG. 1 is a schematic diagram of a magnetic resonance imaging apparatus in one embodiment.

The magnetic resonance imaging apparatus (referred to as "MRI apparatus" hereinbelow) 1 comprises a magnet 2, a table 3, a receive coil 4, and a contrast injection apparatus 5.

The magnet 2 has a reception space 21 in which a subject 14 is received. Moreover, the magnet 2 has a superconductive coil 22, a gradient coil 23, and an RF coil 24. The superconductive coil 22 applies a static magnetic field, the gradient coil 23 applies a gradient pulse, and the RF coil 24 applies an RF pulse. A permanent magnet may be employed in place of the superconductive coil 22.

The table 3 has a cradle 3a for carrying the subject 14. It is by the cradle 3a that the subject 14 is carried into the reception space 21. The receive coil 4 is attached to the subject 14. The receive coil 4 receives magnetic resonance signals from the subject 14.

The contrast injection apparatus 5 injects a contrast medium into the subject 14.

The MRI apparatus 1 further comprises a control section 6, a transmitter 7, a gradient power supply 8, a receiver 9, a processing apparatus 10, a storage section 11, an operating section 12, and a display section 13.

The control section 6 receives from the processing apparatus 10 data containing waveform information, the time for application, etc. of the RF pulse and gradient pulse used in a sequence. The control section 6 then controls the transmitter 7 based on the data for the RF pulse, and controls the gradient power supply 8 based on the data for the gradient pulse. The control section 6 also performs control of the start time for injection of the contrast medium in the contrast injection apparatus 5, control of movement of the cradle 3a, etc. While the control section 6 performs control of the contrast injection apparatus 5, transmitter 7, gradient power supply 8, cradle 3a, etc. in FIG. 1, the control of the contrast injection apparatus 5, transmitter 7, gradient power supply 8, cradle 3a, etc. may be performed by a plurality of control sections. For example, there may be separately provided a control section for controlling the contrast injection apparatus 5, that for controlling the transmitter 7 and gradient power supply 8, and that for controlling the cradle 3a.

The transmitter 7 supplies an electric current to the RF coil 24 based on the data received from the control section 6.

The gradient power supply 8 supplies an electric current to the gradient coil 23 based on the data received from the control section 6.

The receiver 9 applies processing, such as demodulation/detection, to magnetic resonance signals received by the receive coil 4, and outputs the resulting signals to the processing apparatus 10.

Figure 2:
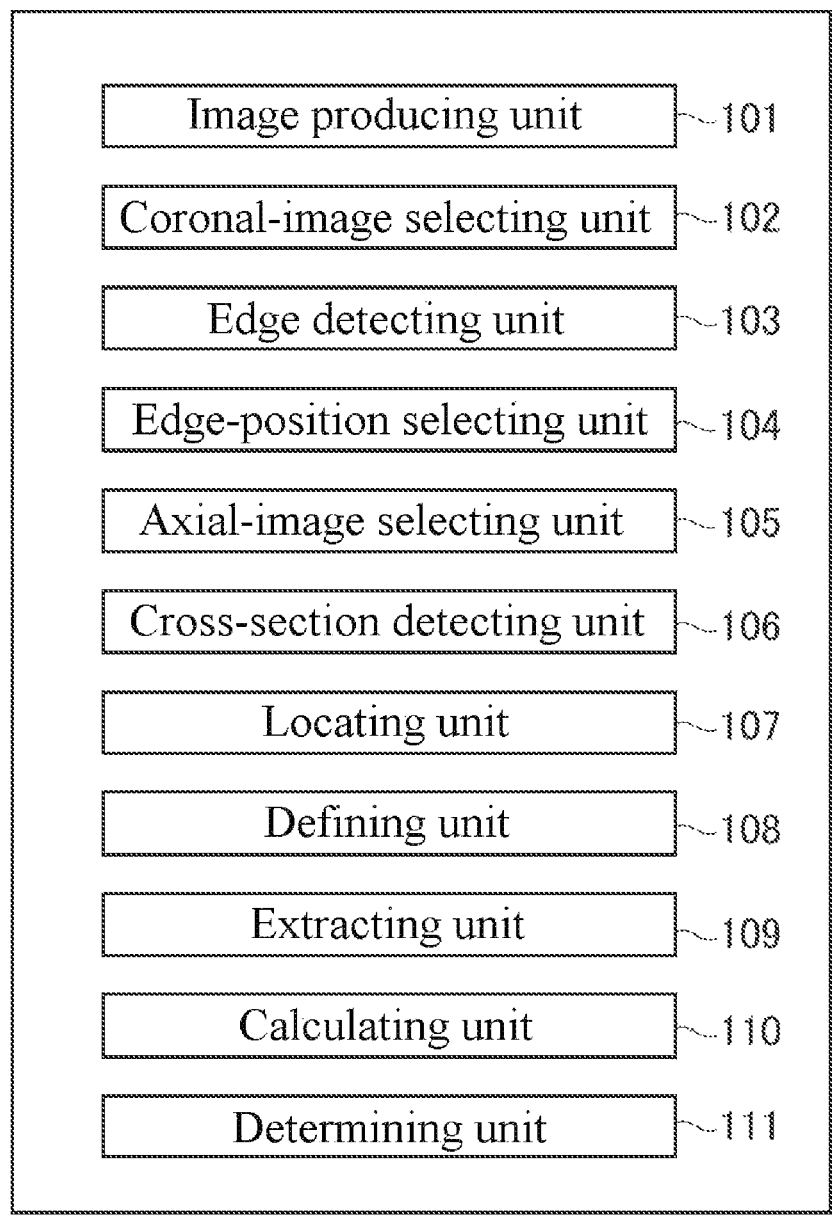
FIG. 2 is an explanatory diagram for a functional block diagram of a processing apparatus.

The storage section 11 stores therein programs executed by the processing apparatus 10, and the like. The storage section 11 may be a non-transitory storage medium, such as a hard disk or CD-ROM. The processing apparatus 10 loads a program stored in the storage section 11, and operates as a processor executing processing written in the program. By executing processing written in the program, the processing apparatus 10 implements several kinds of units. FIG. 2 is an explanatory diagram for a functional block diagram of the processing apparatus 10.

Image producing unit 101 produces an image of a body part to be imaged in the subject 14.

Figure 7:
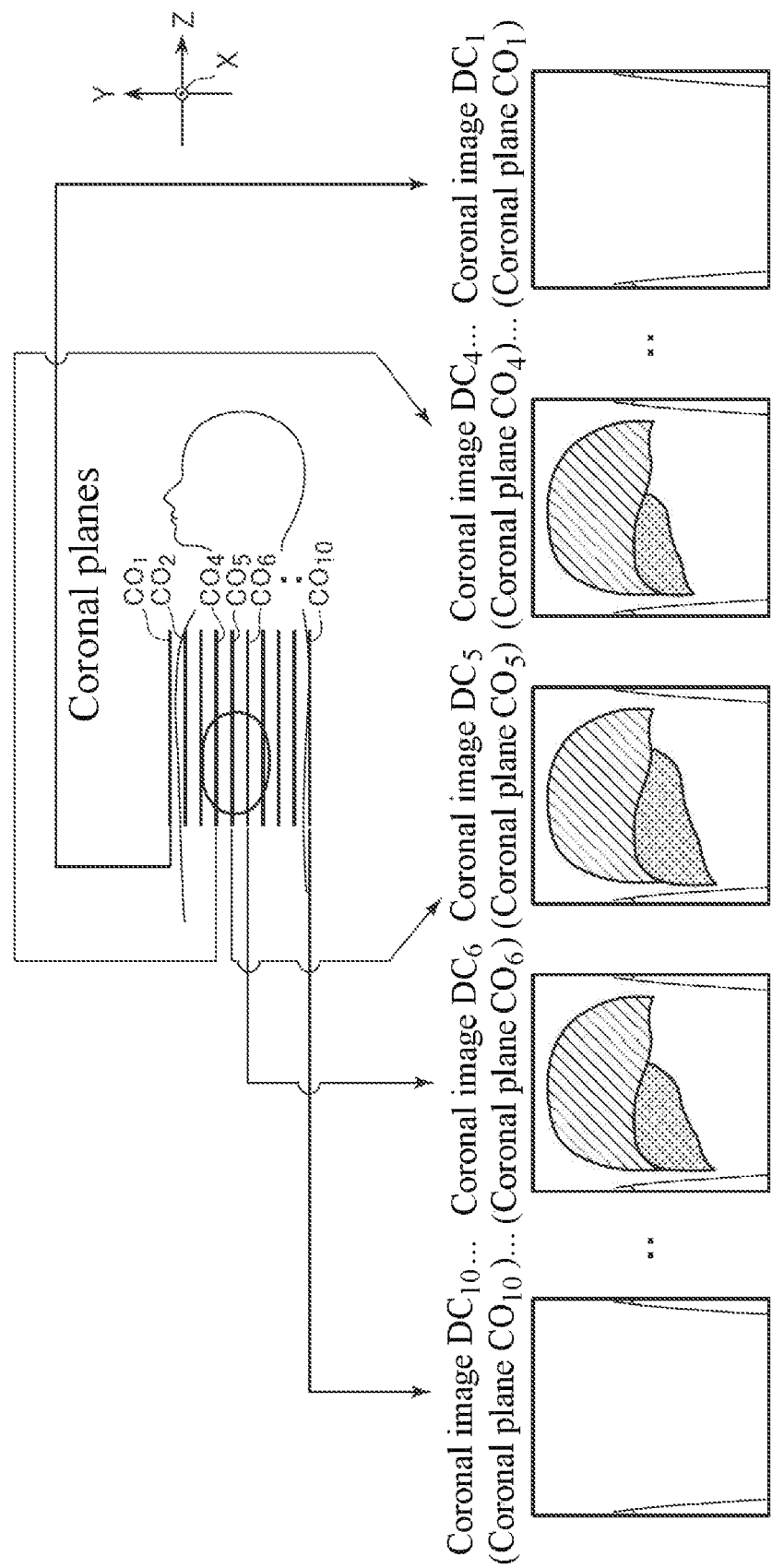
FIG. 7 is a diagram schematically showing images $DC_1$ to $DC_{10}$ in coronal planes $CO_1$ to $CO_{10}$ obtained by the localizer scan LS.

Coronal-image selecting unit 102 selects coronal images intersecting the liver from among coronal images $DC_1$ to $DC_{10}$ (see FIG. 7).

Edge detecting unit 103 detects an edge of the liver adjacent to the lungs in a z-direction for each coronal image selected by the coronal-image selecting unit 102.

Edge-position selecting unit 104 selects a position of the edge of the liver having the largest z-coordinate value.

Figure 12:
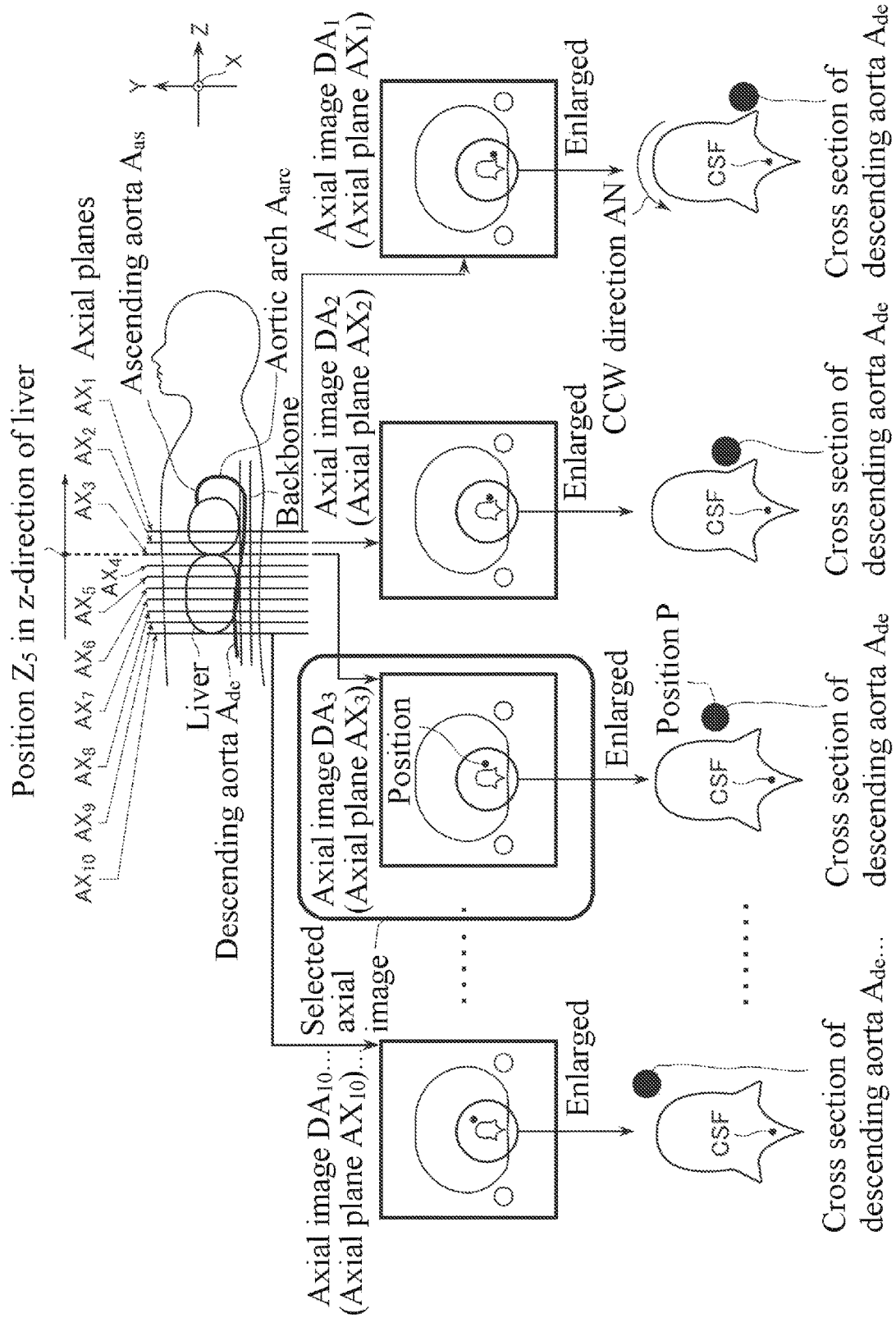
FIG. 12 is a diagram showing axial images selected from among the axial images $DA_1$ to $DA_{10}$.

Axial-image selecting unit 105 selects an axial image closest to the position of the edge of the liver from among axial images $DA_1$ to $DA_{10}$ obtained by a localizer scan LS (see FIG. 12). The axial-image selecting unit 105 constitutes an example of the selecting unit.

Cross-section detecting unit 106 detects a cross section of a descending aorta $A_{de}$ from within the selected axial image.

Figure 13:
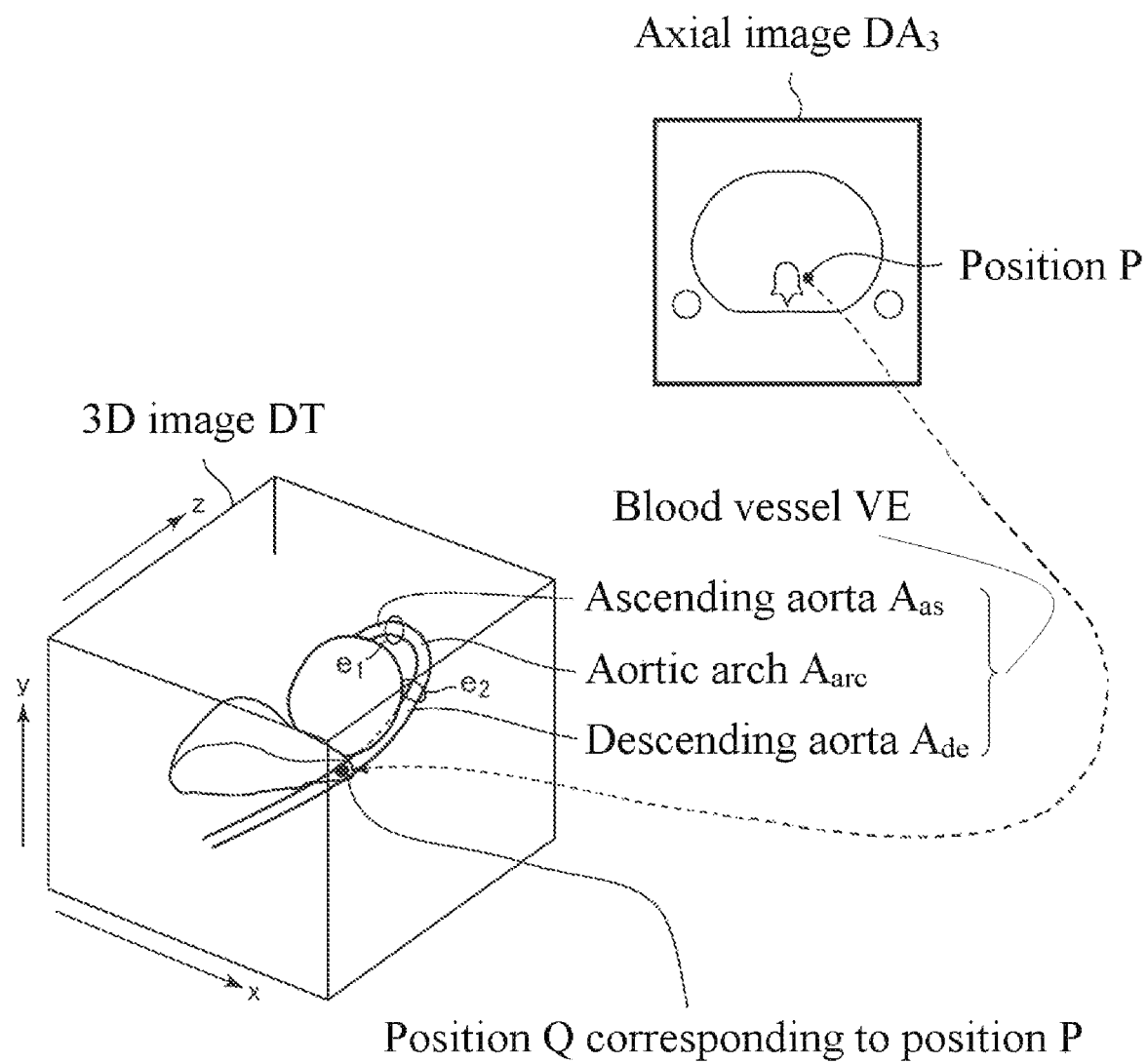
FIG. 13 is an explanatory diagram for step ST7.

Locating unit 107 locates a position Q corresponding to a position P of the cross section of the descending aorta $A_{de}$ from within a 3D image DT (see FIG. 13).

Defining unit 108 defines a slice SL intersecting the 3D image DT. The slice SL will be described in detail with reference to FIGS. 15A, 15B, 15C to 20A, 20B, 20C.

Figure 17A:
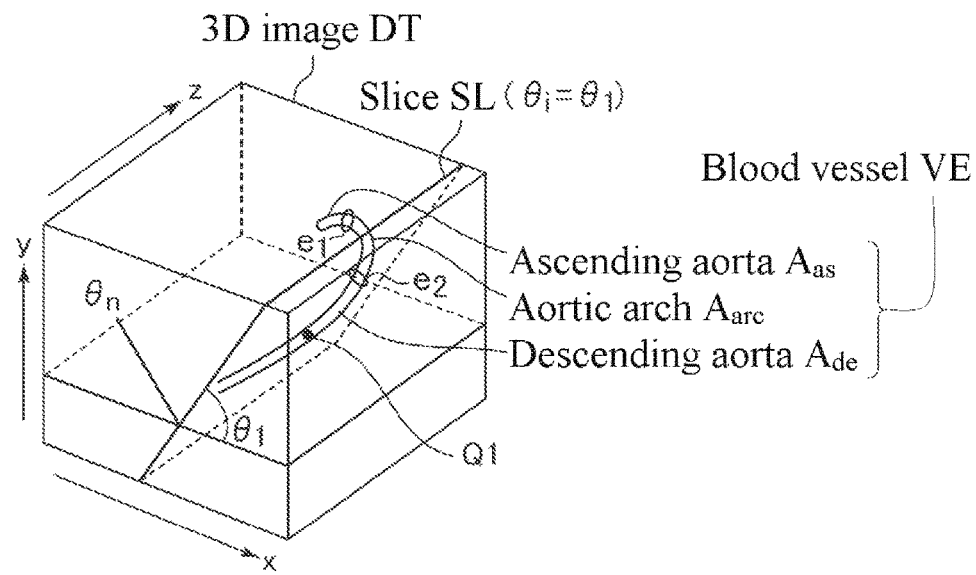
FIGS. 17A-17C are diagrams schematically showing different perspectives of an extracted image portion.
Figure 17B:
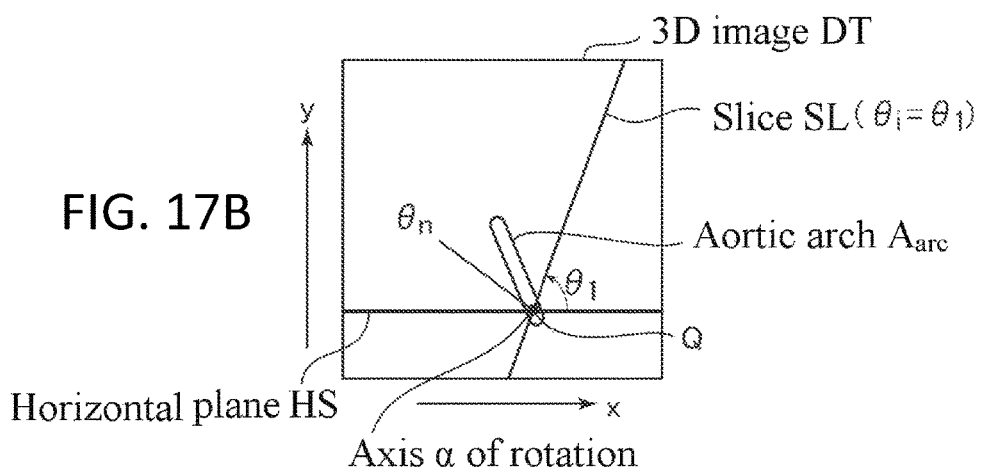
Figure 17C:
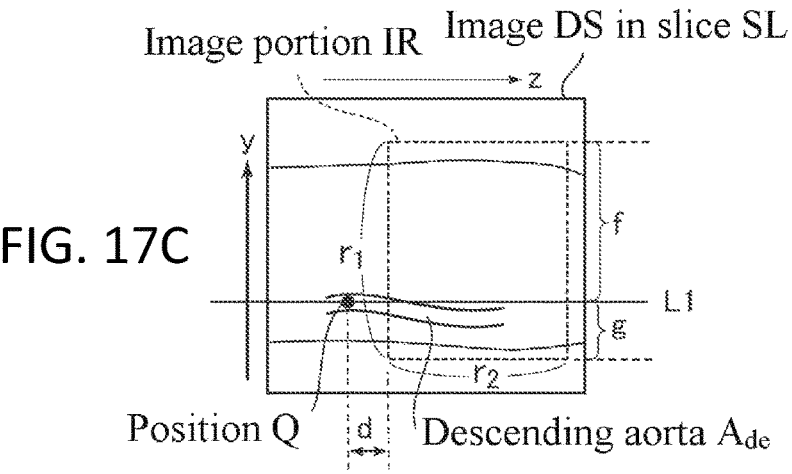

Extracting unit 109 extracts an image portion to which classification processing is to be applied by a classifier C from within an image in the slice SL (see FIGS. 17A, 17B, 17C).

Calculating unit 110 calculates an index VI using the classifier C, which will be discussed later (see FIGS. 18A, 18B, 18C to 20A, 20B, 20C). A combination of the extracting unit 109 and calculating unit 110 constitutes an example of the unit for obtaining an index.

Determining unit 111 determines an angle of the slice SL at which the slice SL contains a blood vessel to be detected based on a result of the calculation by the calculating unit 110.

The MRI apparatus 1 comprises a computer including the processing apparatus 10. The processing apparatus 10 implements the image producing unit 101 to determining unit 111, etc. by loading programs stored in the storage section 11. The processing apparatus 10 may implement the image producing unit 101 to determining unit 111 by a single processor, or by two or more processors. The programs executed by the processing apparatus 10 may be stored in a single storage section, or separately in a plurality of storage sections. The processing apparatus 10 constitutes an example of the blood vessel detection apparatus.

Referring back to FIG. 1, the description will be continued. The operating section 12 is operated by an operator to input several kinds of information. The display section 13 displays several kinds of information. The MRI apparatus 1 is configured as described above.

Figure 4:
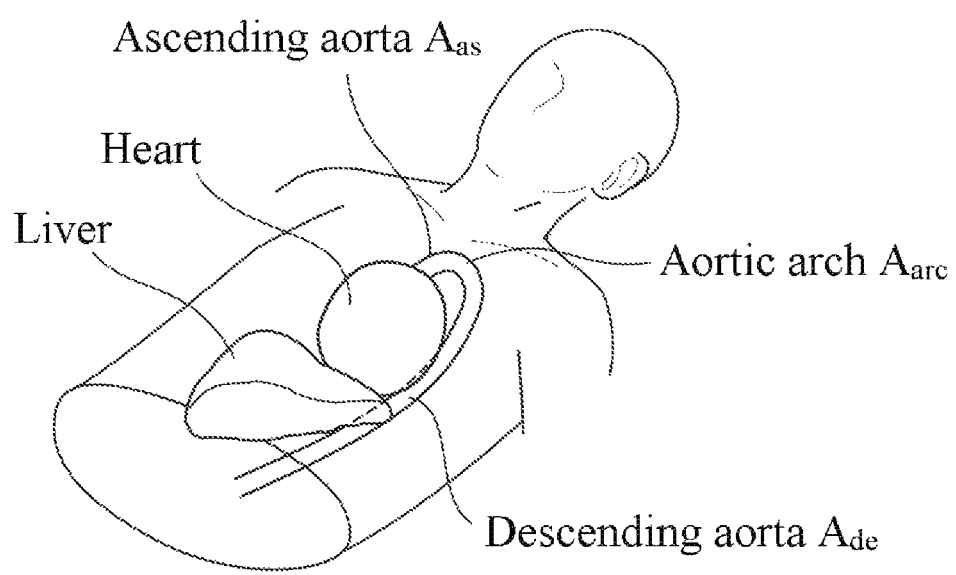
FIG. 4 is a diagram schematically showing a body part to be imaged.

FIG. 3 is a diagram showing scans performed in the present embodiment, and FIG. 4 is a diagram schematically showing a body part to be imaged.

In the present embodiment, a localizer scan LS, a 3D data acquisition scan AS, a main scan MS, etc. are performed.

The localizer scan LS is a scan for acquiring an image of a body part including the liver and descending aorta $A_{de}$. The image obtained in the localizer scan LS is used for locating a position z5 of the edge of the liver in the z-direction (see FIG. 11), and a position P of the cross section of the descending aorta $A_{de}$ (see FIG. 12). A method of locating these positions will be discussed later.

The 3D data acquisition scan AS is a scan for obtaining a 3D image of a body part including the ascending aorta $A_{as}$, aortic arch $A_{arc}$, and descending aorta $A_{de}$.

The main scan MS is a scan for obtaining an image of a body part including the liver. In the main scan MS, a contrast medium is injected into the subject, and an imaging sequence for acquiring an image of the liver is performed. Now an exemplary operational flow in the MRI apparatus in performing the localizer scan LS, 3D data acquisition scan AS, and main scan MS will be described below.

Figure 5:
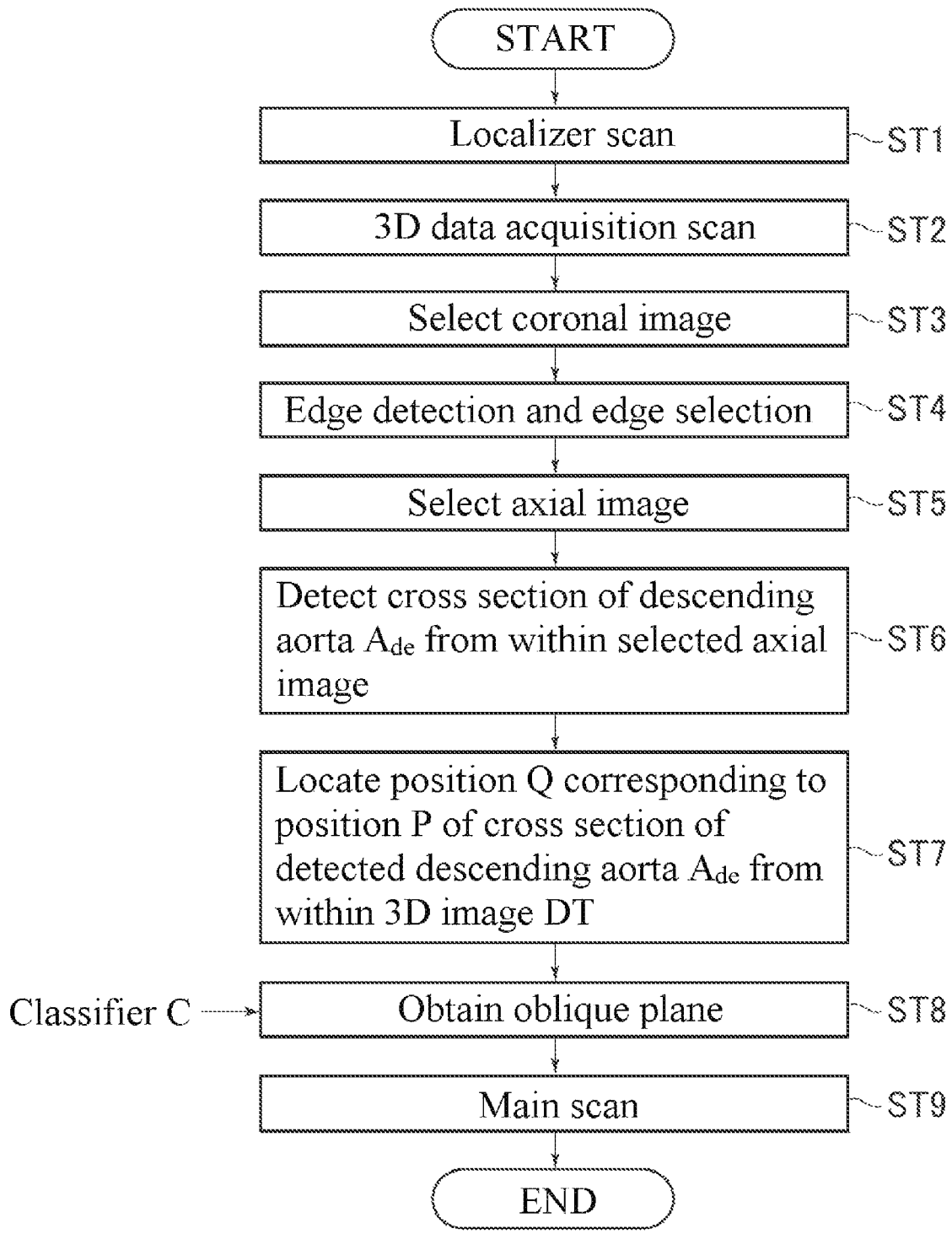
FIG. 5 is a diagram showing an exemplary operational flow in the MRI apparatus.

FIG. 5 is a diagram showing an exemplary operational flow in the MRI apparatus. At step ST1, a localizer scan LS (see FIG. 3) is performed.

The localizer scan LS is a 2D scan for acquiring an image of a body part including the liver and descending aorta $A_{de}$.

In performing the localizer scan LS, the control section 6 (see FIG. 1) sends data for an RF pulse in a sequence used in the localizer scan LS to the transmitter 7, and data for a gradient pulse in the sequence used in the localizer scan LS to the gradient power supply 8. The transmitter 7 supplies an electric current to the RF coil 24 based on the data received from the control section 6, while the gradient power supply 8 supplies an electric current to the gradient coil 23 based on the data received from the control section 6. Thus, the RF coil 24 applies an RF pulse, while the gradient coil 23 applies a gradient pulse. By performing the localizer scan LS, an MR signal is generated from the imaged body part. The MR signal is received by the receive coil 4 (see FIG. 1). The receive coil 4 receives the MR signal and outputs an analog signal containing information on the MR signal. The receiver 9 applies signal processing, such as demodulation/detection, to the signal received from the receive coil 4, and outputs data resulting from the signal processing to the processing apparatus 10.

Figure 6:
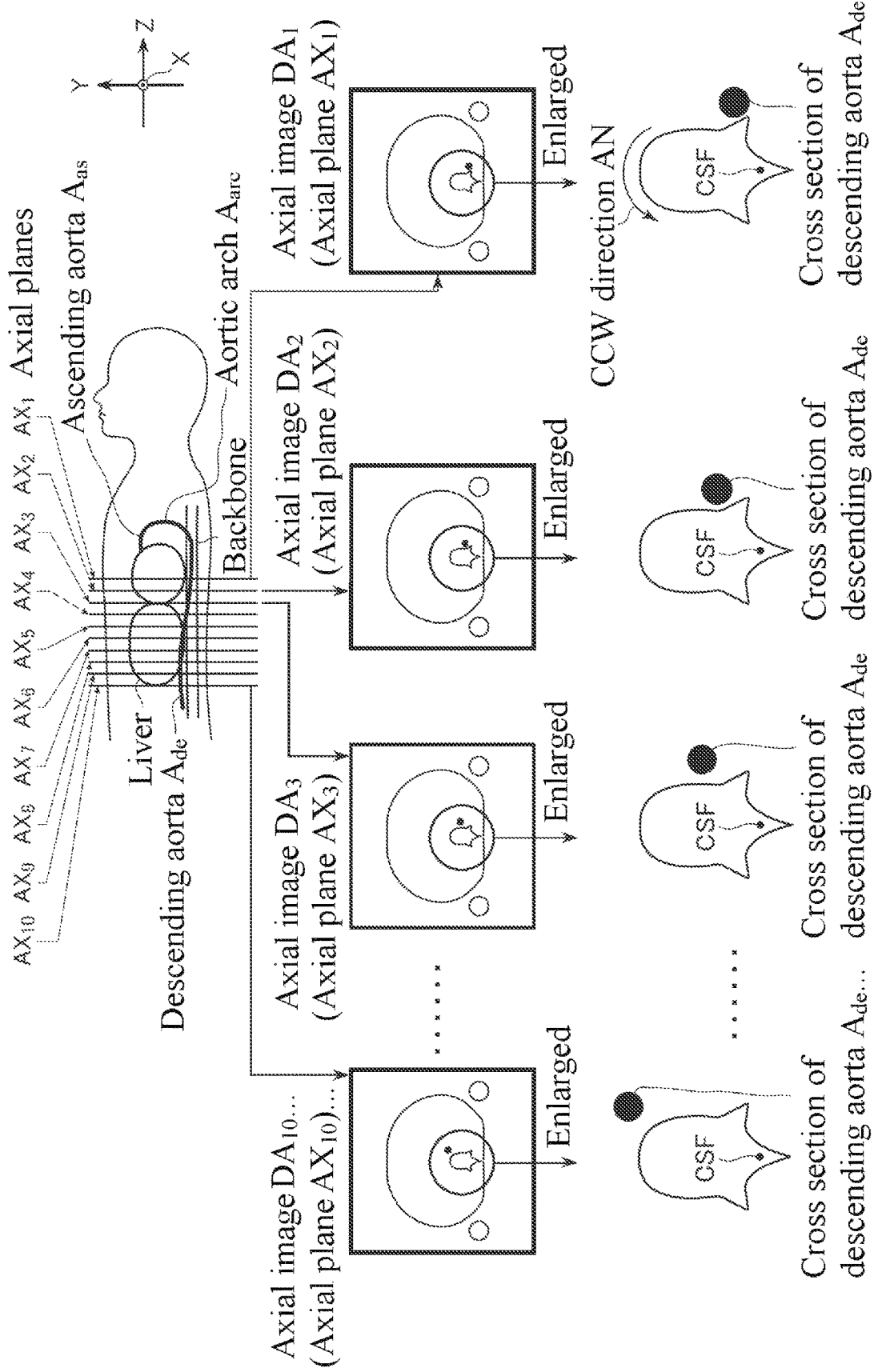
FIG. 6 is a diagram schematically showing images $DA_1$ to $DA_{10}$ in axial planes $AX_1$ to $AX_{10}$ obtained by a localizer scan LS.

The image producing unit 101 (see FIG. 2) produces images in axial, sagittal, and coronal planes based on the data collected by the localizer scan LS. FIG. 6 is a diagram schematically showing images $DA_1$ to $DA_{10}$ in axial planes $AX_1$ to $AX_{10}$ obtained by the localizer scan LS, and FIG. 7 is a diagram schematically showing images $DC_1$ to $DC_{10}$ in coronal planes $CO_1$ to $CO_{10}$ obtained by the localizer scan LS (wherein images in sagittal planes are omitted in the drawings for convenience of explanation). While FIG. 6 shows a case of ten axial planes and FIG. 7 shows a case of ten coronal planes, the numbers of axial planes and coronal planes (and sagittal planes) are not limited to ten and they may be more than or less than ten. In FIGS. 6 and 7, x-, y-, and z-directions correspond respectively to RL, AP, and SI directions. The axial planes $AX_1$ to $AX_{10}$ are arranged in the z-direction, while the coronal planes $CO_1$ to $CO_{10}$ are arranged in the y-direction. An image in the axial plane will be referred to as "axial image," and that in the coronal plane as "coronal image" hereinbelow.

In FIG. 6, axial images $DA_1$, $DA_2$, $DA_3$, and $DA_{10}$ of the axial images $DA_1$ to $DA_{10}$ are schematically shown. Since the axial planes $AX_1$ to $AX_{10}$ each intersect the descending aorta $A_{de}$, a cross section of the descending aorta $A_{de}$ is rendered in the axial images $DA_1$ to $DA_{10}$.

In FIG. 7, on the other hand, coronal images $DC_1$, $DC_4$, $DC_5$, $DC_6$, and $DC_{10}$ of the coronal images $DC_1$ to $DC_{10}$ are schematically shown. The coronal images $DC_1$ to $DC_{10}$ include coronal images (e.g., $DC_4$, $DC_5$, and $DC_6$) each containing a cross section of the liver and coronal images (e.g., $DC_1$ and $DC_{10}$) not intersecting the liver.

After performing the localizer scan LS, the flow goes to step ST2. At step ST2, a 3D data acquisition scan AS is performed.

Figure 8:
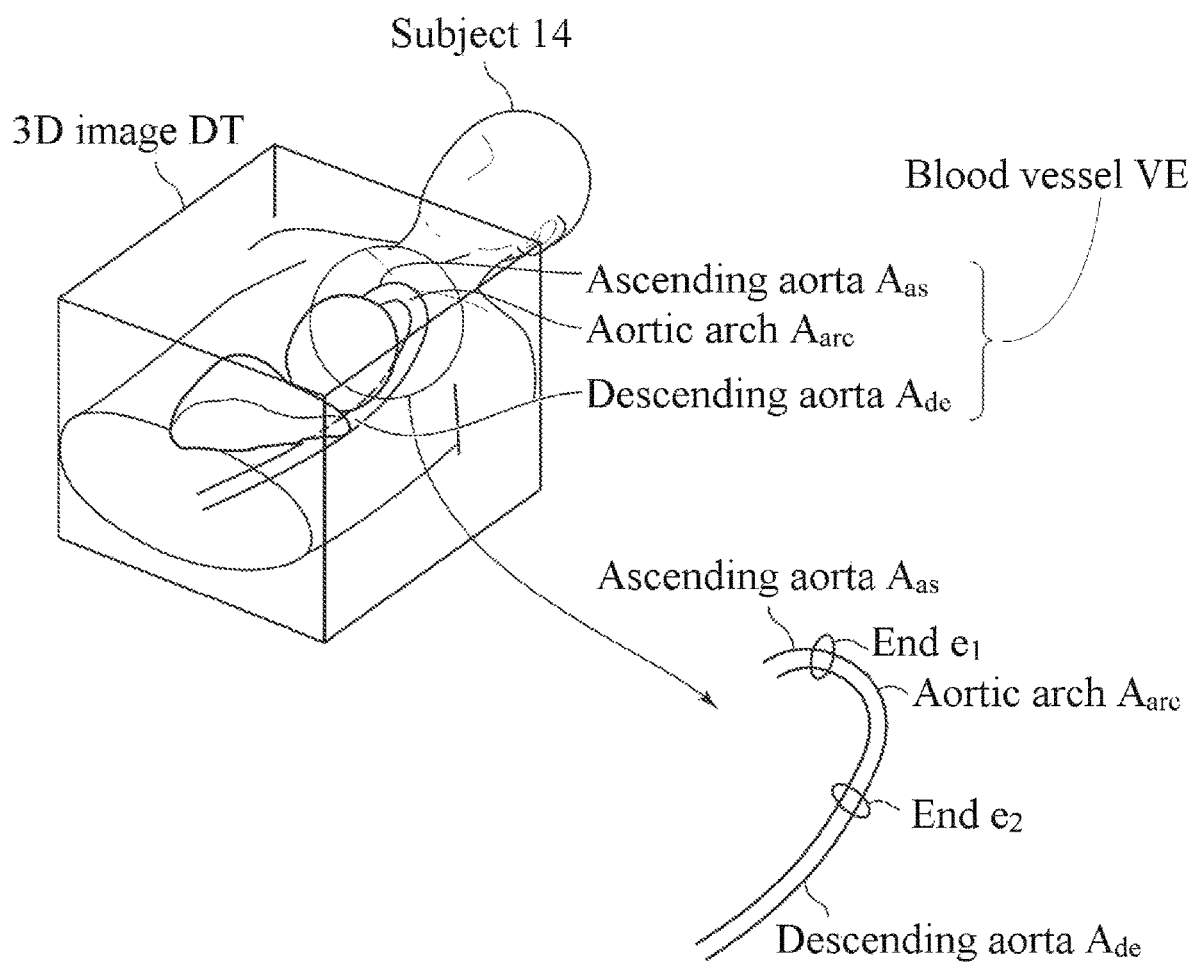
FIG. 8 is a diagram schematically showing a body part on which a 3D data acquisition scan AS is performed.

FIG. 8 is a diagram schematically showing a body part on which the 3D data acquisition scan AS is performed.

The 3D data acquisition scan AS is a 3D scan for acquiring an image of a body part containing a blood vessel VE including the ascending aorta $A_{as}$, aortic arch $A_{arc}$, and descending aorta $A_{de}$, and its surrounding organs. By performing the 3D scan, a 3D image DT of the body part including the aortic arch $A_{arc}$ may be obtained. An end e1 of the aortic arch $A_{arc}$ leads to the ascending aorta $A_{as}$, while an end e2 of the aortic arch $A_{arc}$ leads to the descending aorta $A_{de}$.

FIGS. 9A, 9B, 9C and 10A, 10B, 10C are diagrams for schematically explaining a relative positional relationship between the ascending aorta $A_{as}$, aortic arch $A_{arc}$, and descending aorta $A_{de}$ contained in the 3D image DT. It should be noted that in FIGS. 9A, 9B, 9C and 10A, 10B, 10C, organs, such as the liver and heart, are omitted in the drawings for convenience of explanation.

Figure 9A:
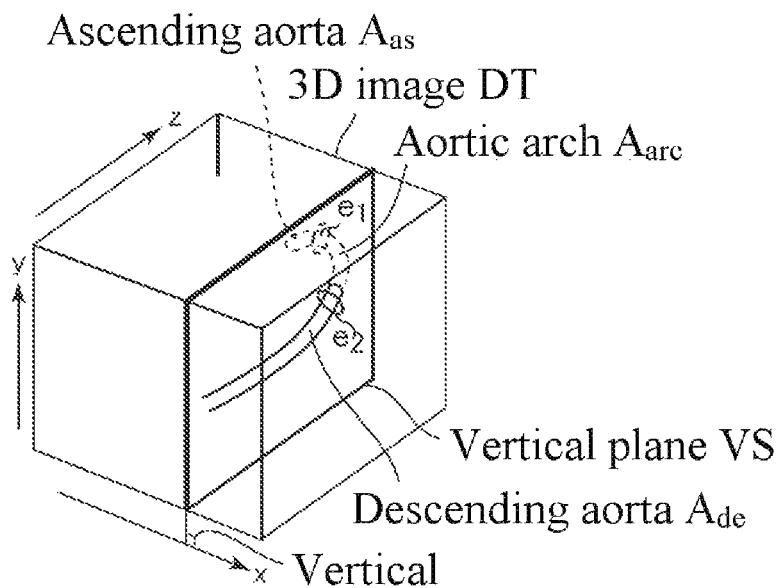
FIGS. 9A-9C are diagrams showing different perspectives of a vertical plane VS intersecting a 3D image DT.
Figure 9B:
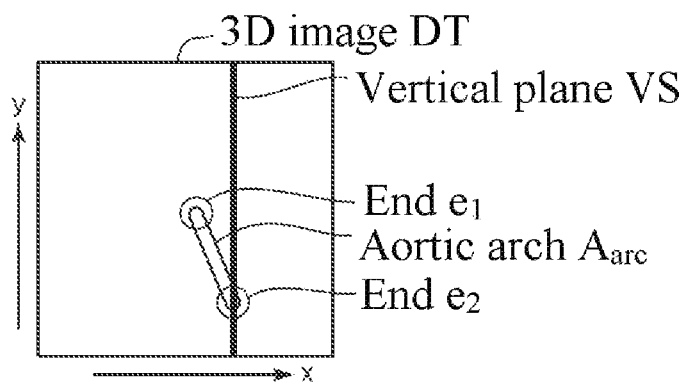
Figure 9C:
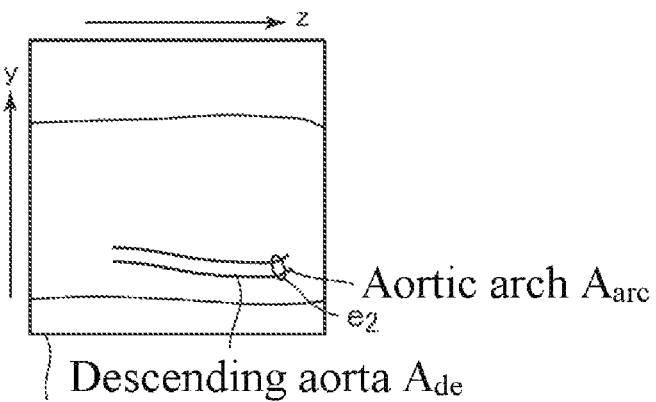

First, FIGS. 9A, 9B, 9C will be described. FIGS. 9A-9C are diagrams showing different perspectives of a vertical plane VS intersecting a 3D image DT.

FIG. 9A is a perspective view of the 3D image DT, and FIG. 9B is a view of the 3D image DT in the z-direction. A vertical plane VS intersecting the 3D image DT is shown in FIG. 9A and FIG. 9B. FIG. 9C is a diagram schematically showing a cross-sectional image DV in the vertical plane VS.

The vertical plane VS is a plane that is parallel to the y- and z-directions and vertical to the x-direction. The descending aorta $A_{de}$ and the end e2 of the aortic arch $A_{arc}$ lie within (or in the vicinity of) the vertical plane VS. However, since the aortic arch $A_{arc}$ is oblique with respect to the y-direction, the end e1 of the aortic arch $A_{arc}$ lies offset from the vertical plane VS (see a2). It can thus be seen that the cross-sectional image DV of the vertical plane VS (see a3) contains the descending aorta $A_{de}$ and the end e2 of the aortic arch $A_{arc}$, but does not contain the end e1 of the aortic arch $A_{arc}$ and the ascending aorta $A_{as}$.

Figure 10A:
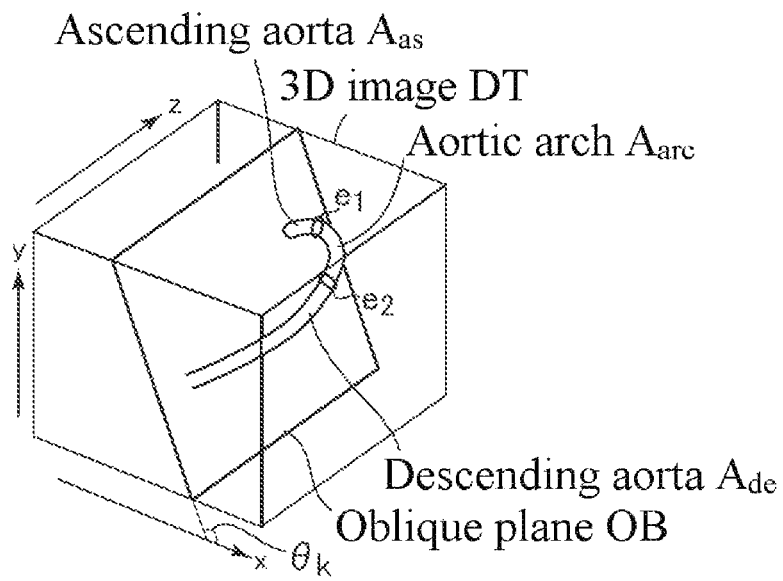
FIGS. 10A-10C are diagrams showing different perspectives of an oblique plane OB intersecting the 3D image DT.
Figure 10B:
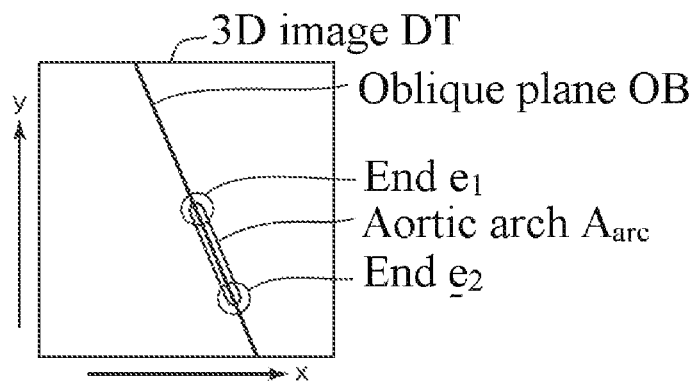
Figure 10C:
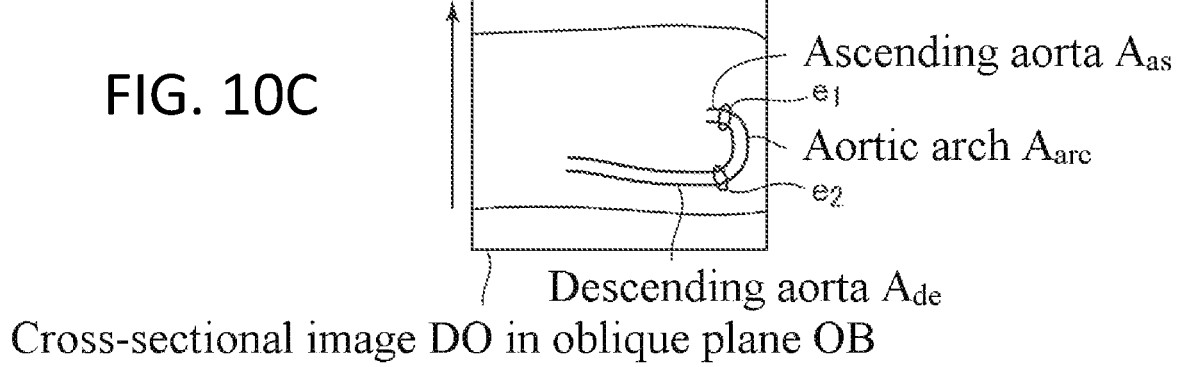

Next, FIGS. 10A, 10B, 10C will be described. FIGS. 10A-10C are diagrams showing different perspectives of an oblique plane OB intersecting the 3D image DT.

FIG. 10A is a perspective view of the 3D image DT, and FIG. 10B is a view of the 3D image DT in the z-direction. An oblique plane OB intersecting the 3D image DT is shown in FIG. 10A and FIG. 10B. FIG. 10C is a diagram schematically showing a cross-sectional image DO in the oblique plane OB.

The aortic arch $A_{arc}$ is oblique with respect to the y-direction. Therefore, when a plane (oblique plane) OB intersecting the 3D image DT at an angle $\theta_k$ that is oblique with respect to the x-axis is considered, the oblique plane OB intersects the 3D image DT longitudinally cutting the ascending aorta $A_{as}$, aortic arch $A_{arc}$, and descending aorta $A_{de}$. The value of $\theta_k$ is typically 95° to 120°, for example.

It can thus be seen that the aortic arch $A_{arc}$ has a curved shape within the oblique plane OB at the angle $\theta_k$ and leads to the ascending aorta $A_{as}$ and descending aorta $A_{de}$.

After performing the 3D data acquisition scan AS for acquiring the 3D image DT, the flow goes to step ST3.

Figure 11:
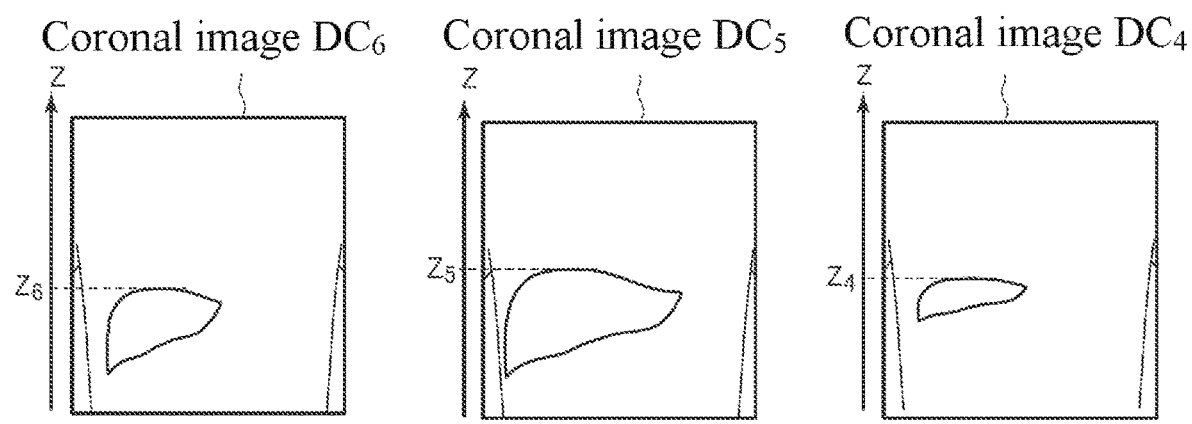
FIG. 11 is a diagram schematically showing selected coronal images $DC_4$, $DC_5$, and $DC_6$.

At step ST3, the coronal-image selecting unit 102 (see FIG. 2) selects coronal images intersecting the liver among the coronal images $DC_1$ to $DC_{10}$ (see FIG. 7) obtained at step ST1. For the method of selecting coronal images intersecting the liver, a method described in paragraph [0038] in the disclosure of Japanese Patent Application KOKAI No. 2016-059397, for example, may be employed. In the present embodiment, it is assumed that the coronal-image selecting unit 102 selects three coronal images $DC_4$, $DC_5$, and $DC_6$ as the coronal images intersecting the liver for convenience of explanation. FIG. 11 schematically shows the selected coronal images $DC_4$, $DC_5$, and $DC_6$. After selecting the coronal images, the flow goes to step ST4.

At step ST4, the edge detecting unit 103 (see FIG. 2) detects an edge of the liver adjacent to the lungs in the z-direction for each of the selected coronal images $DC_4$, $DC_5$, and $DC_6$. As the edge detection method, a method described in paragraphs [0041] to [0071] in the disclosure of Japanese Patent Application KOKAI No. 2016-059397, for example, may be employed. In FIG. 11, the positions of the detected edge of the liver are designated by $z_4$, $z_5$, and $z_6$.

After detecting the edge of the liver, the edge-position selecting unit 104 (see FIG. 2) selects a position of the edge having the largest z-coordinate value from among the positions $z_4$, $z_5$, and $z_6$ of the detected edge of the liver in the z-direction for each of the coronal images $DC_4$, $DC_5$, and $DC_6$. It is assumed here that the z-coordinate $z_5$ of the edge detected from within the coronal image $DC_5$ is largest. Therefore, the edge-position selecting unit 104 selects $z_5$ as the position of the edge having the largest z-coordinate value. After selecting $z_5$, the flow goes to step ST5.

At step ST5, the axial-image selecting unit 105 (see FIG. 2) selects an axial image that is closest to the position $z_5$ of the edge of the liver selected at step ST4 from among the axial images $DA_1$ to $DA_{10}$ (see FIG. 6) obtained by the localizer scan LS. FIG. 12 shows an axial image selected from among the axial images $DA_1$ to $DA_{10}$. It is assumed here that the axial image $DA_3$ is closest to the position $z_5$ of the edge of the liver. Therefore, the axial-image selecting unit 105 selects the axial image $DA_3$. After selecting the axial image $DA_3$, the flow goes to step ST6.

At step ST6, the cross-section detecting unit 106 (see FIG. 2) detects a cross section of the descending aorta $A_{de}$ from within the axial image $DA_3$ selected at step ST5. For the method of detecting a cross section of the descending aorta $A_{de}$ from within the axial image $DA_3$, a method described in the disclosure of Japanese Patent Application KOKAI No. 2015-123306 may be employed. In FIG. 12, the position of the cross section of the descending aorta $A_{de}$ detected from within the axial image $DA_3$ is designated by the symbol "P." After detecting the cross section of the descending aorta $A_{de}$, the flow goes to step ST7.

FIG. 13 is an explanatory diagram for step ST7. At step ST7, the locating unit 107 (see FIG. 2) locates a position Q corresponding to the position P of the cross section of the descending aorta $A_{de}$ in the axial image $DA_3$, from within the 3D image DT produced at step ST2. The position Q of the cross section of the descending aorta $A_{de}$ may thus be located from within the 3D image DT. After locating the position Q, the flow goes to step ST8.

At step ST8, the oblique plane OB (see FIGS. 10A, 10B, 10C) longitudinally cutting the blood vessel VE is obtained based on the position Q of the descending aorta $A_{de}$ located at step ST7. Now a method of obtaining the oblique plane OB will be described below.

In the present embodiment, the oblique plane OB is obtained using a classifier C for classifying the blood vessel VE. The classifier C is created beforehand prior to imaging of the subject. Now a method of creating the classifier C will be briefly described.

Figure 14:
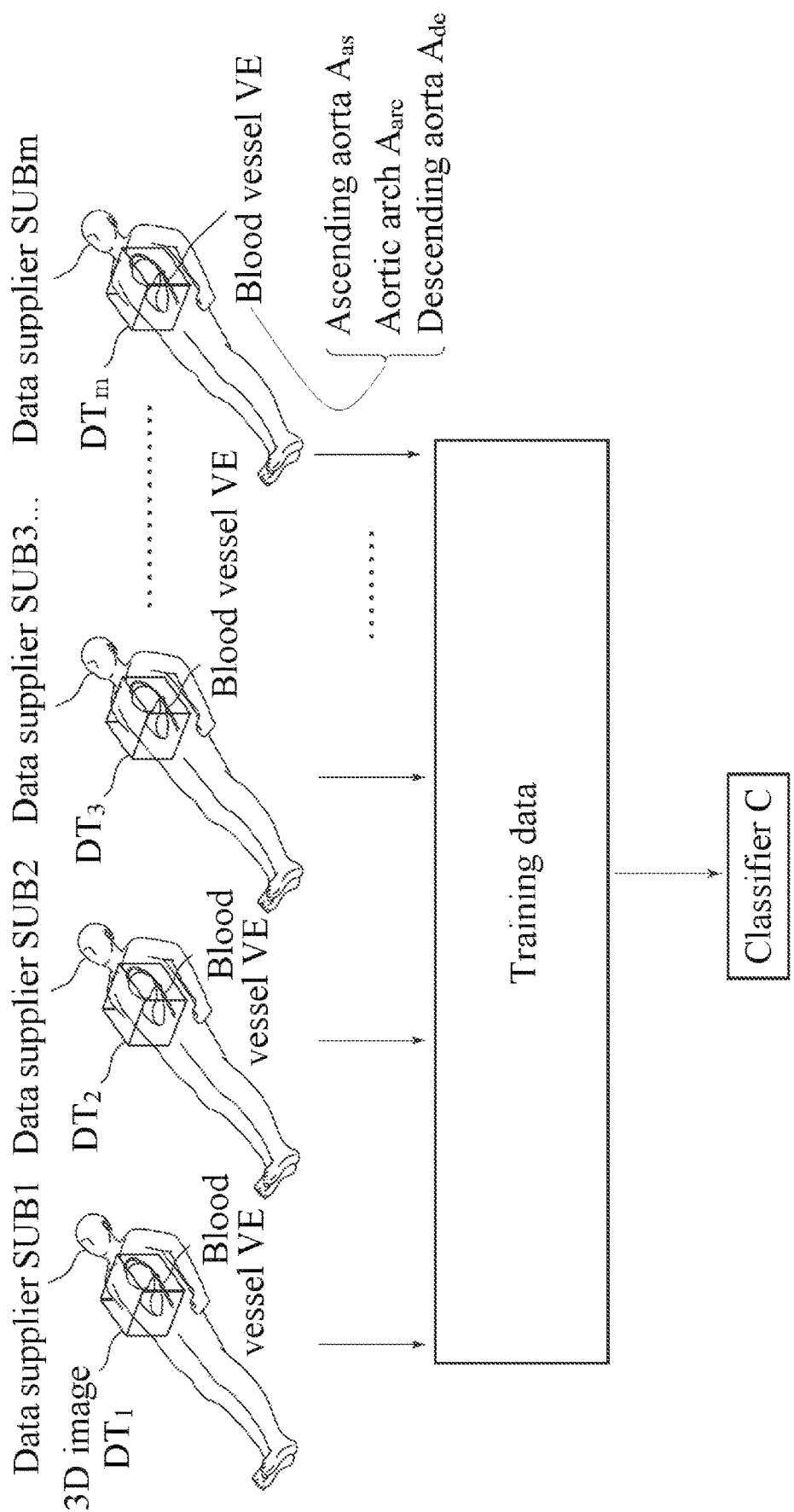
FIG. 14 is an explanatory diagram for a method of creating a classifier C.

FIG. 14 is an explanatory diagram for the method of creating a classifier C.

In the present embodiment, from 3D images $DT_1$ to $DT_m$ of the torsos of a plurality of data donors $SUB_1$ to $SUB_m$, image portions usable as training data are extracted. The training data includes the following data, for example: (1) data representing a cross section of a blood vessel VE including the ascending aorta $A_{as}$, aortic arch $A_{arc}$, and descending aorta $A_{de}$; (2) data including only a partial cross section of the blood vessel VE (for example, data including a cross section of the ascending aorta $A_{as}$ and not including cross sections of the aortic arch $A_{arc}$ and descending aorta $A_{de}$, or data including a cross section of the descending aorta $A_{de}$ and not including cross sections of the aortic arch $A_{arc}$ and ascending aorta $A_{as}$); and (3) data not including the blood vessel VE.

By learning the training data using a machine learning technique, a classifier C for classifying the blood vessel VE is created.

At step ST8, the thus-created classifier C is used to obtain the oblique plane OB (see FIGS. 10A, 10B, 10C) longitudinally cutting the blood vessel VE of the subject 14. Now step ST8 will be described referring to FIGS. 15A, 15B, 15C to 20A, 20B, 20B.

Figure 15A:
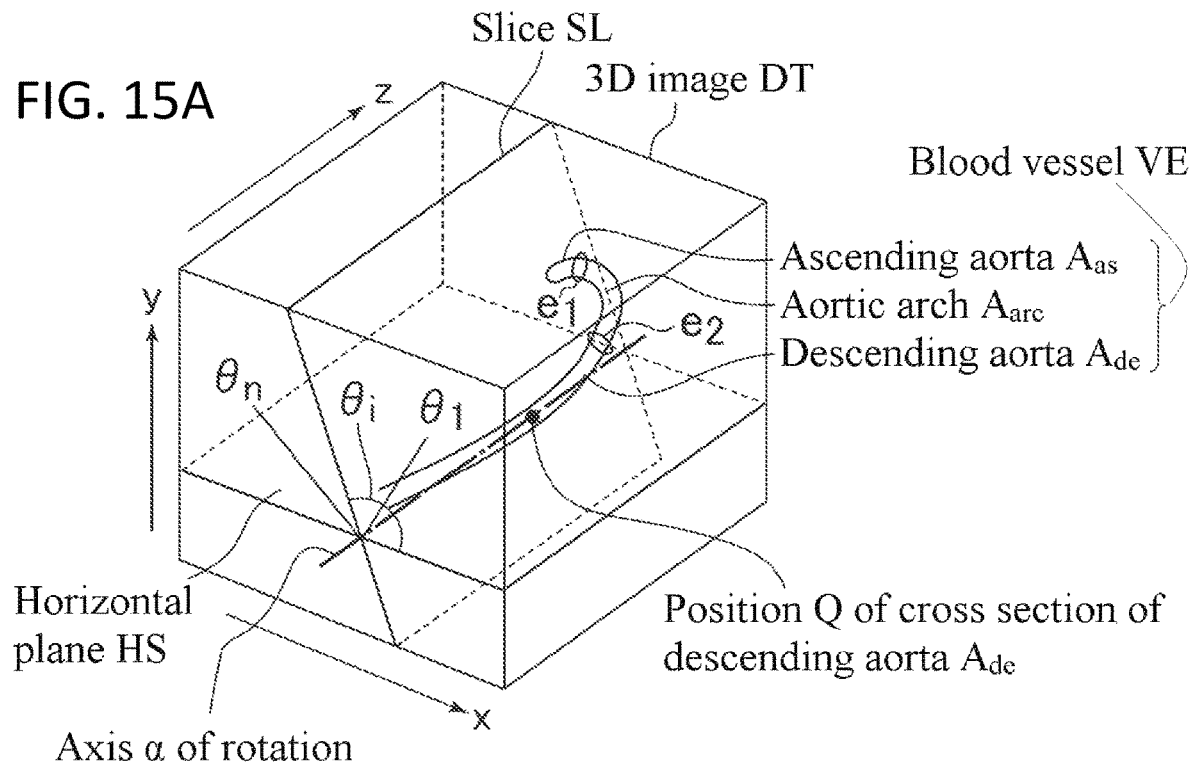
FIGS. 15A and 15B are diagrams schematically showing different perspectives of a slice SL intersecting the 3D image DT.
Figure 15B:
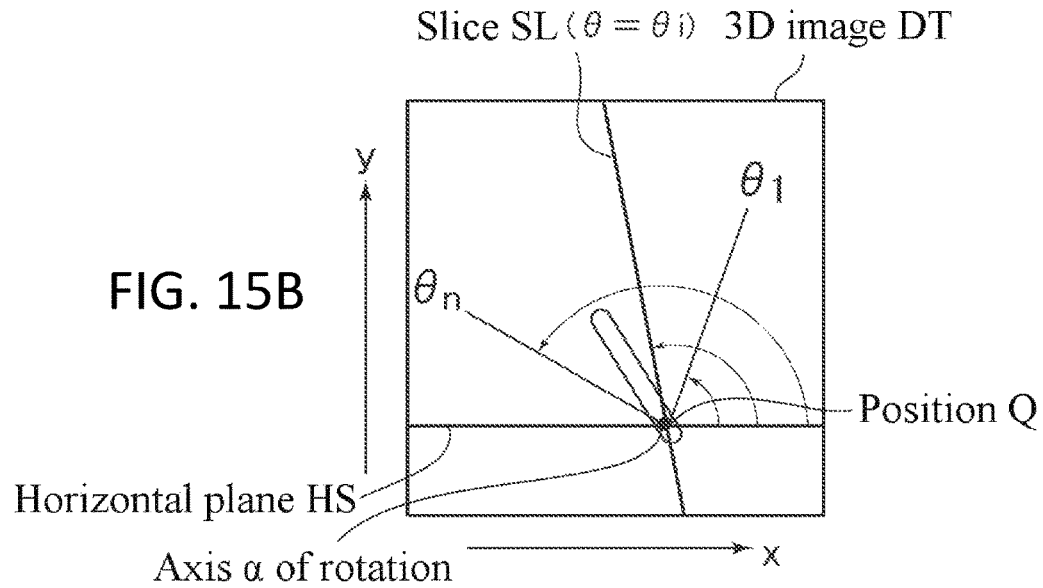

At step ST8, the defining unit 108 (see FIG. 2) first defines a slice intersecting the 3D image DT of the subject 14 (see FIGS. 15A, 15B, 15C).

FIGS. 15A and 15B are diagrams schematically showing different perspectives of a slice SL intersecting the 3D image DT.

FIG. 15A is a perspective view of the 3D image DT of the subject 14, and FIG. 15B is a view of the 3D image DT of the subject 14 in the z-direction.

The defining unit 108 defines the slice SL. The slice SL is defined to pass through the position Q of the cross section of the descending aorta $A_{de}$ and to be parallel to the z-direction. The thickness t of the slice SL may be set taking account of the diameter of the blood vessel VE to be detected. Assuming that the blood vessel VE to be detected has a diameter of the order of 1 cm, for example, t may be set to have a value of the order of t=1 cm to 1.5 cm, for example. It should be noted that FIGS. 15A, 15B, 15C represent the slice SL as a square shape in order to express the slice SL by a simple geometric shape. Therefore, it should be noted that although not expressed in FIGS. 15A, 15B, 15C, the thickness t of the slice L is actually set taking account of the diameter of the blood vessel VE.

The defining unit 108 rotates the slice SL around an axis $\alpha$ of rotation passing through the position Q in parallel with the z-direction. It is assumed here that the defining unit 108 rotates the slice SL around the axis $\alpha$ of rotation so that the angle $\theta_i$ of the slice SL is changed within a specific angular range $\theta_1 \le \theta_i \le \theta_n$ (wherein the angle $\theta_i$ of the slice SL is defined as an angle formed between the slice SL and a horizontal plane HS). The angular range $\theta_1 \le \theta_i \le \theta_n$ is set taking account of the standard shape of the blood vessel VE, the standard size of the blood vessel VE, the standard position of the blood vessel VE relative to the heart, etc. The angle $\theta_1$ may be set to $\theta_1=60°$, for example, and $\theta_n$ may be set to $\theta_n=135°$, for example.

Now a case in which the defining unit 108 sets the angle $\theta_i$ of the slice SL to $\theta_i=\theta_1$ will be first described.

Figure 16A:
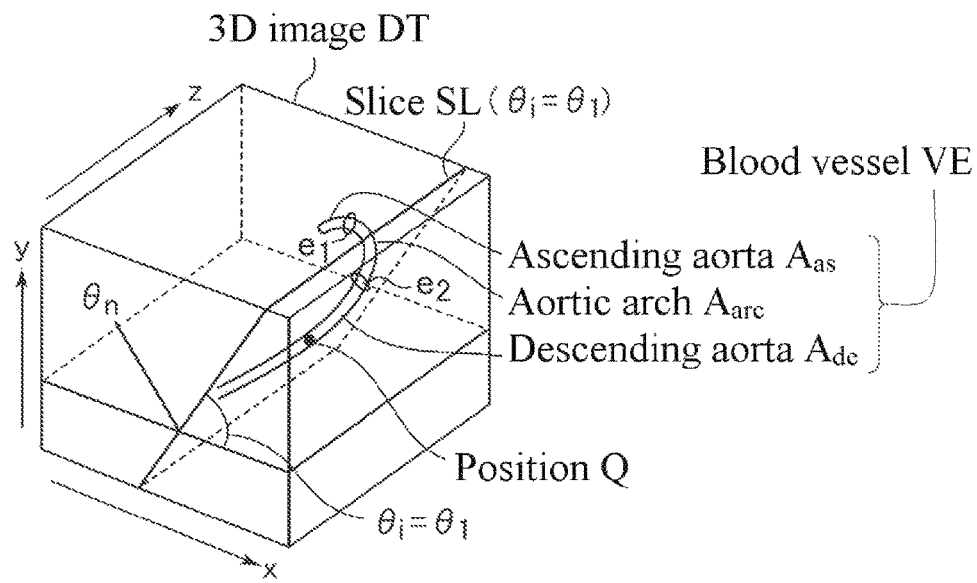
FIGS. 16A-16C are explanatory diagrams showing different perspectives for a case in which an angle $\theta_i$ of the slice SL is set to $\theta_i=\theta_1$.
Figure 16B:
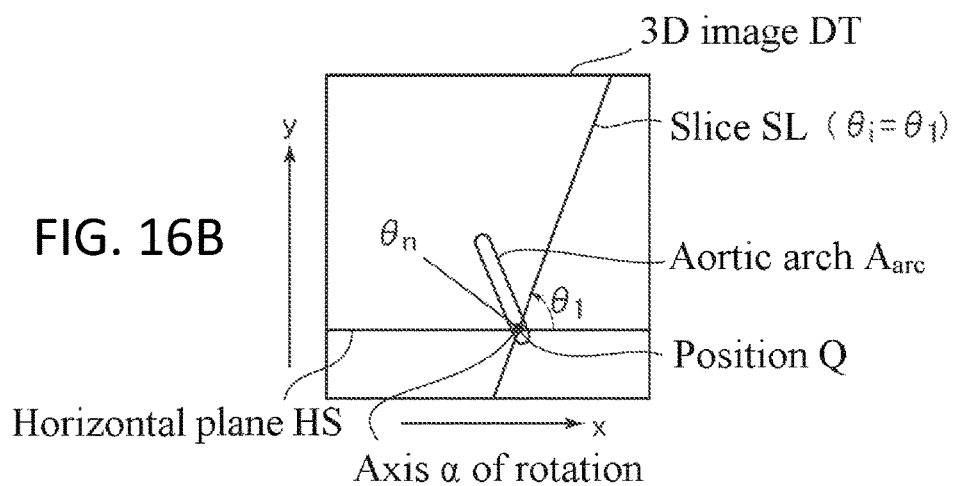
Figure 16C:
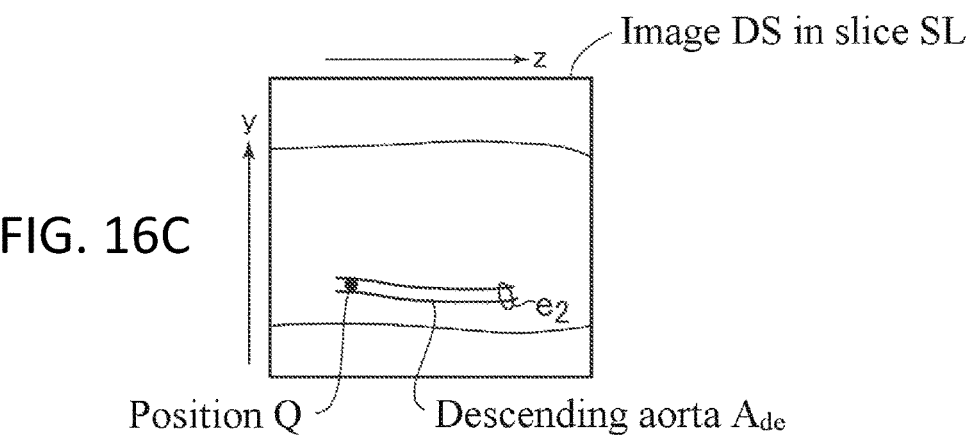

FIGS. 16A-16C are explanatory diagrams showing different perspectives for a case in which an angle $\theta_i$ of the slice SL is set to $\theta_i=\theta_1$.

FIG. 16A is a perspective view of the 3D image DT of the subject 14, FIG. 16B is a view of the 3D image DT of the subject 14 in the z-direction, and FIG. 16C is a diagram schematically showing an image DS in the slice SL at $\theta_i=\theta_1$.

The image DS in the slice SL shown in (a3) is an image that may be obtained by, for example, arithmetically averaging values of voxels within the slice SL in a direction of the thickness of the slice SL. After setting the angle $\theta_i$ of the slice SL to $\theta_i=\theta_1$, the extracting unit 109 (see FIG. 2) extracts an image portion to which classification processing by the classifier C is to be applied from within the image (see a3) in the slice SL (see FIGS. 17A, 17B, 17C).

FIGS. 17A-17C are diagrams schematically showing different perspectives of an extracted image portion. The extracting unit 109 extracts an image portion IR with reference to the position Q of the cross section of the descending aorta $A_{de}$ (see FIG. 17C). Sides r1 and r2 of the image portion IR are determined beforehand taking account of the standard size of the blood vessel VE. The sides r1 and r2 may be set to have a length corresponding to 40 pixels to 100 pixels, for example.

Moreover, the side r1 is set to have a ratio of f:g with respect to a line L1 passing through the position Q of the cross section of the descending aorta $A_{de}$ in parallel with the z-direction. The ratio f:g in the side r1 of the image portion IR is also determined beforehand taking account of the standard size of the blood vessel VE. The ratio f:g may be f:g=4:1, for example.

Furthermore, the side r1 of the image portion IR is positioned at a distance d from the position Q of the cross section of the descending aorta $A_{de}$ in the z-direction. The value of d is, again, determined beforehand taking account of the standard size of the blood vessel VE.

Figure 18A:
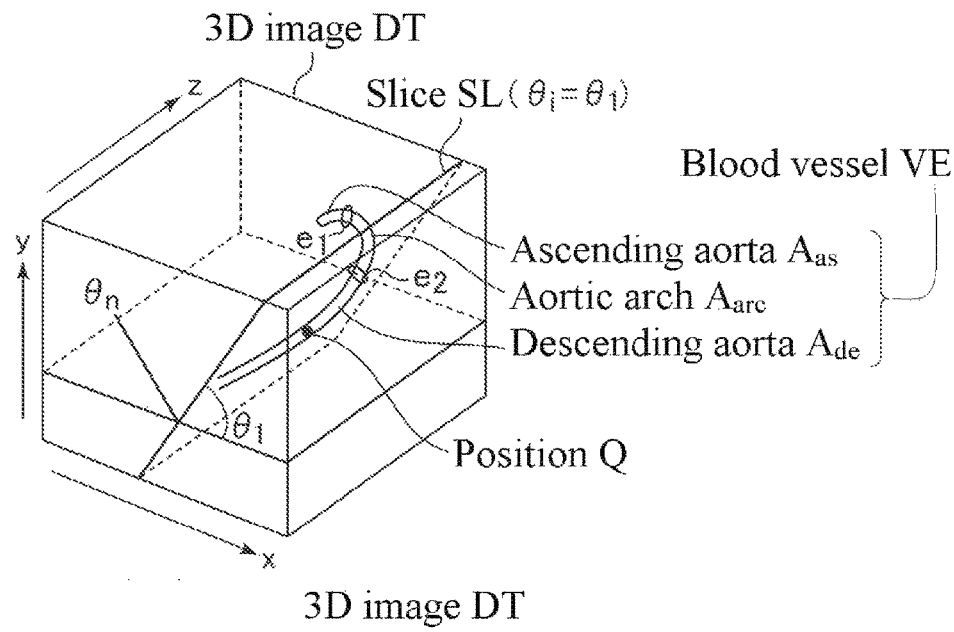
FIGS. 18A-18C are explanatory diagrams showing different perspectives for a method of deciding whether or not a blood vessel VE to be detected is contained in the slice SL.
Figure 18B:
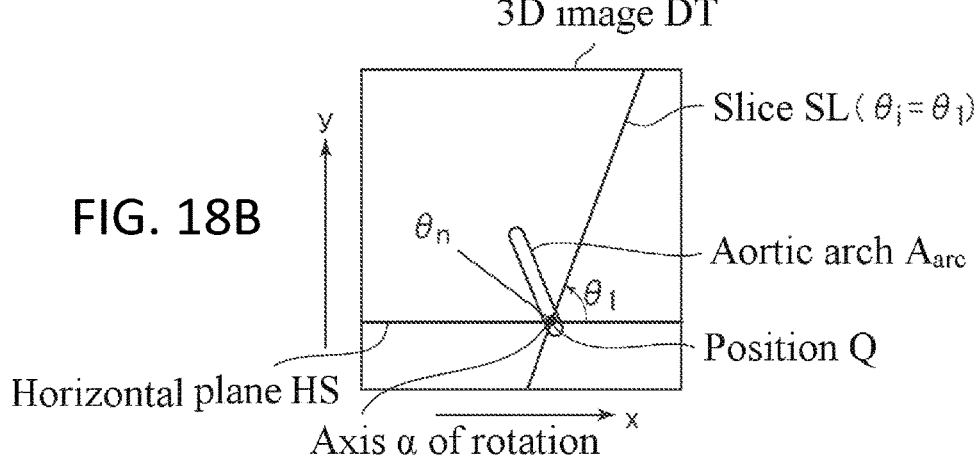
Figure 18C:
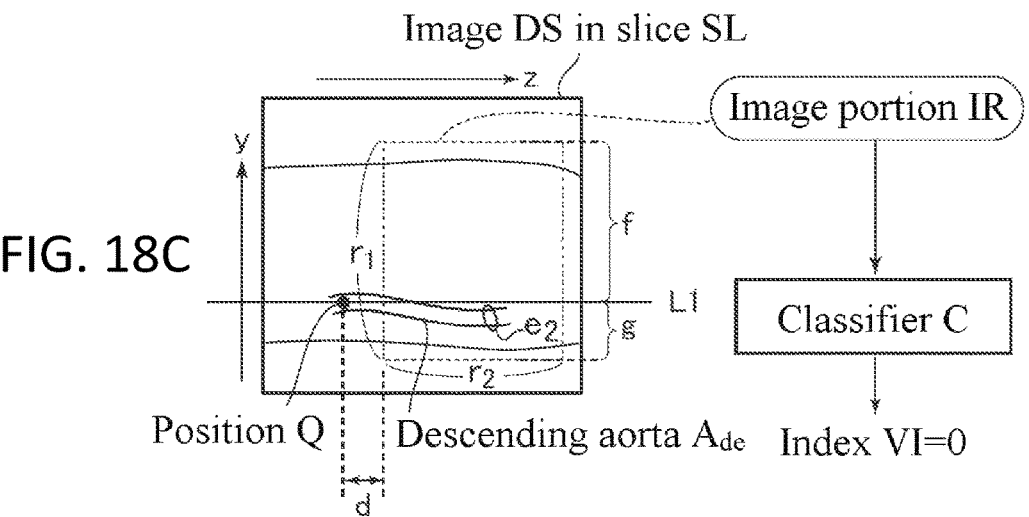

After extracting the image portion IR from the image DS in the slice SL, it is decided whether or not the blood vessel VE to be detected is contained in the slice SL based on the extracted image portion IR (see FIGS. 18A, 18B, 18C).

FIGS. 18A-18C are explanatory diagrams showing different perspectives for a method of deciding whether or not a blood vessel VE to be detected is contained in the slice SL.

The calculating unit 110 (see FIG. 2) uses the classifier C to obtain an index VI for deciding whether or not the blood vessel VE to be detected is contained in the slice SL. Specifically, the calculating unit 110 executes classification processing for classifying the blood vessel VE to be detected using the classifier C in the extracted image portion IR. In the present embodiment, the classifier C decides that the blood vessel VE to be detected is contained in the slice SL when the whole blood vessel VE is contained in the image portion IR, while it decides that the blood vessel VE to be detected is not contained in the slice SL when only part or none of the blood vessel VE is contained in the image portion IR. When the classifier C decides that the blood vessel VE to be detected is contained in the slice SL, it outputs one as the value of the index VI, while when it decides that the blood vessel VE to be detected is not contained in the slice SL, it outputs zero as the value of the index VI. It is thus possible to determine whether or not the blood vessel VE is contained in the slice SL. While the image portion IR contains the descending aorta $A_{de}$ and the end e2 of the aortic arch $A_{arc}$ in FIGS. 18A, 18B, 18C, it does not contain the portion on the side of the end e1 of the aortic arch $A_{arc}$ and the ascending aorta $A_{as}$. Therefore, the value of the index VI that the classifier C outputs is zero at $\theta=\theta_1$. Thus, the determining unit 111 (see FIG. 2) determines that the slice SL does not contain the blood vessel VE to be detected at $\theta=\theta_1$.

Next, the defining unit 108 changes the value of the angle $\theta_i$ of the slice SL from $\theta_1$ to $\theta_2$.

Figure 19A:
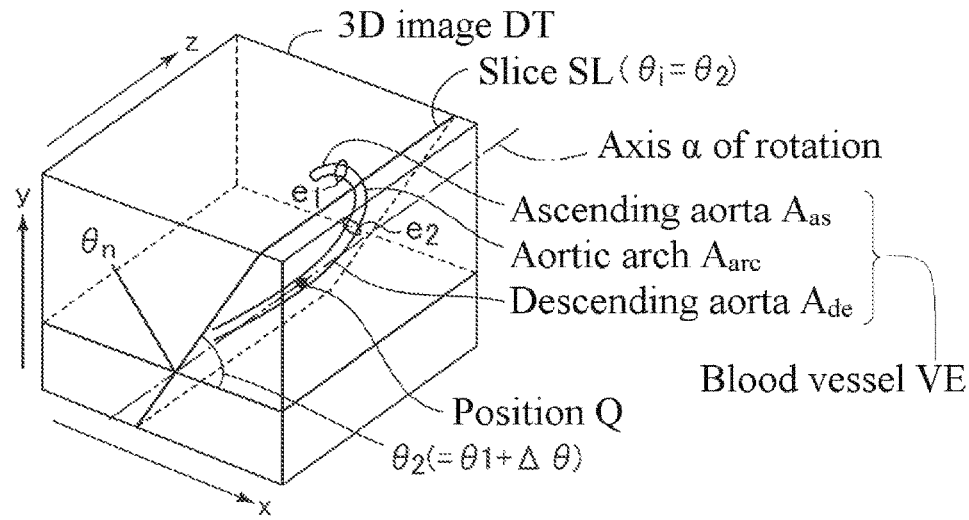
FIGS. 19A-19C are explanatory diagrams showing different perspectives when $\theta_i=\theta_2$.
Figure 19B:
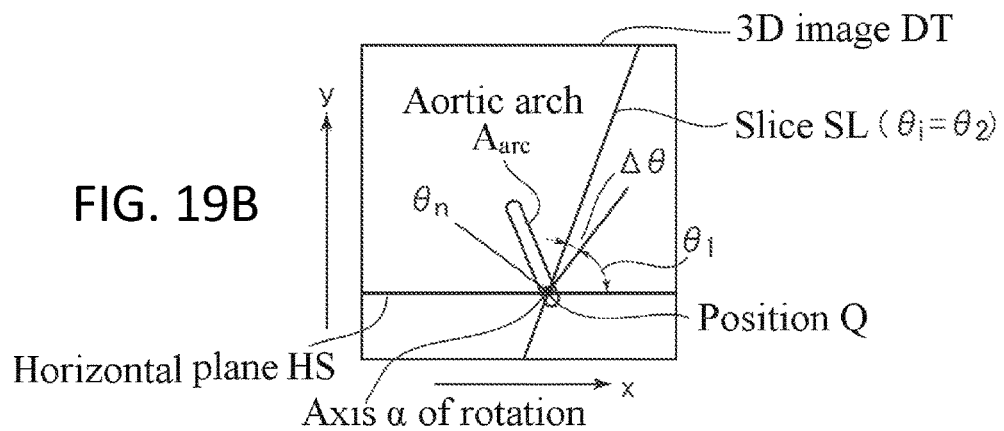
Figure 19C:
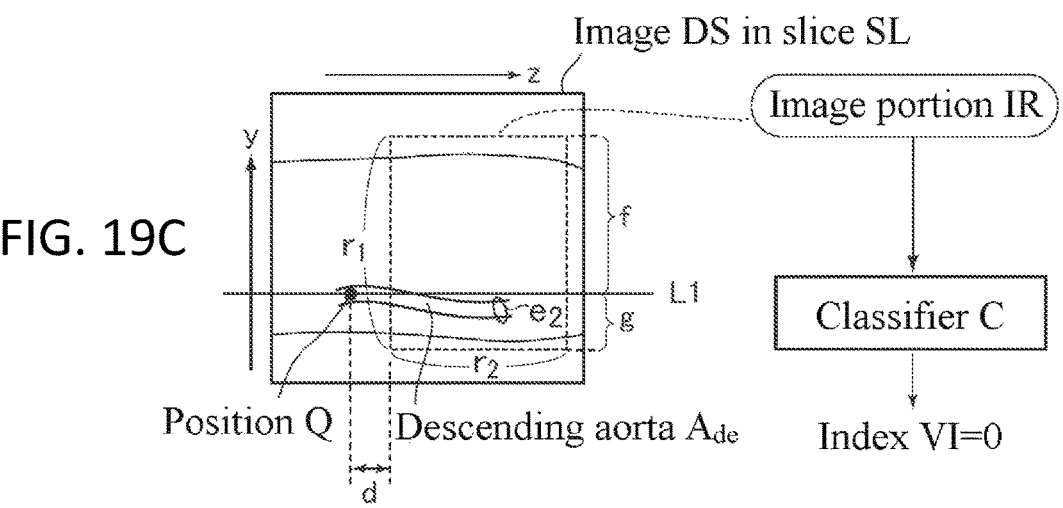

FIGS. 19A-19C are explanatory diagrams showing different perspectives when $\theta_i=\theta_2$. The defining unit 108 rotates the slice SL around the axis $\alpha$ of rotation by $\Delta\theta$ from $\theta_1$. This changes the angle $\theta_i$ of the slice SL from $\theta_1$ to $\theta_2$ ($=\theta_1+\Delta\theta$). The extracting unit 109 extracts an image portion IR from the image DS in the slice SL at $\theta_2$. The calculating unit 110 then uses the classifier C to calculate an index VI representing whether or not the blood vessel VE is contained in the slice SL at $\theta_2$. Similarly to $\theta_1$, VI=0 at $\theta_2$ because not the whole range of the blood vessel VE is contained in the image portion IR. Therefore, the determining unit 111 determines that the slice SL does not contain the blood vessel VE to be detected at $\theta=\theta_2$.

Similarly thereafter, the angle $\theta_i$ of the slice SL is changed within an angular range of $\theta_1 \leq \theta_i \leq \theta_n$, and each time the angle $\theta_i$ of the slice SL is changed, it is determined whether or not the blood vessel VE to be detected is contained. Therefore, an angle $\theta_i$ of the slice SL at which the slice SL contains the blood vessel VE to be detected may be determined from within the angular range $\theta_1$ to $\theta_n$.

Figure 20A:
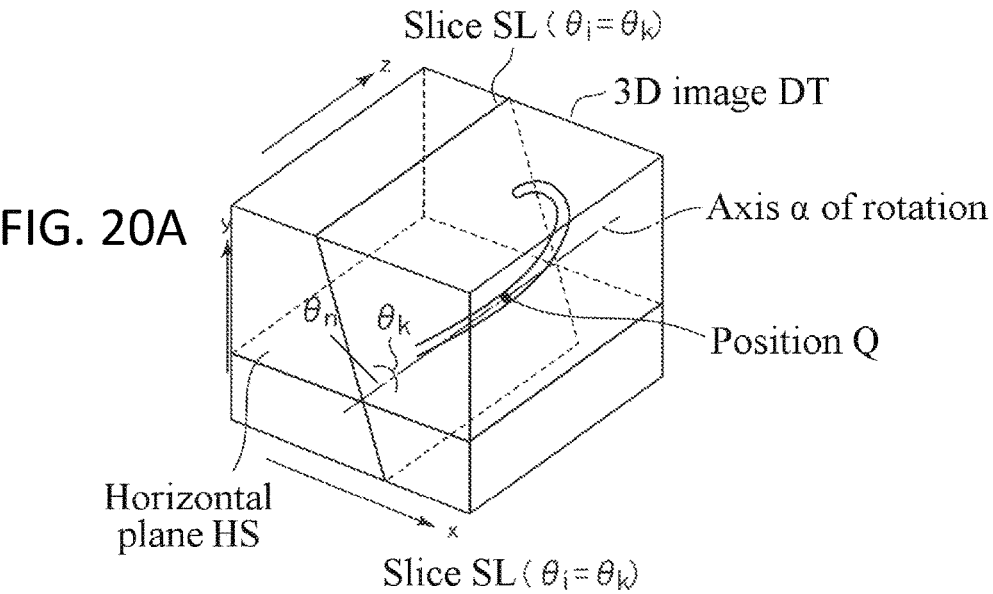
FIGS. 20A-20C are explanatory diagrams showing different perspectives when $\theta_i=\theta_k$.
Figure 20B:
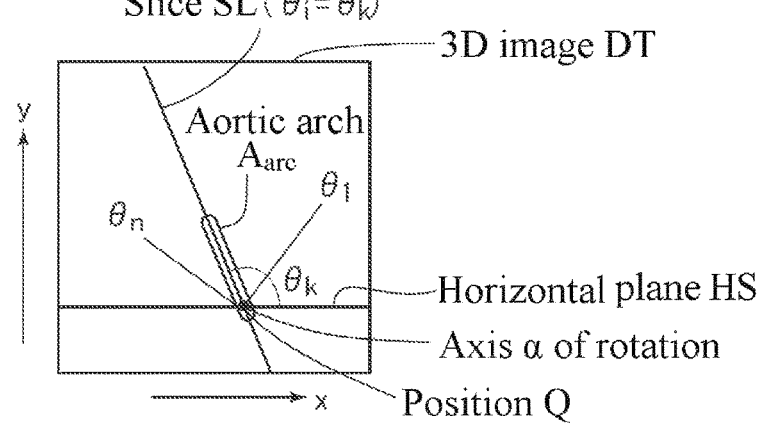
Figure 20C:
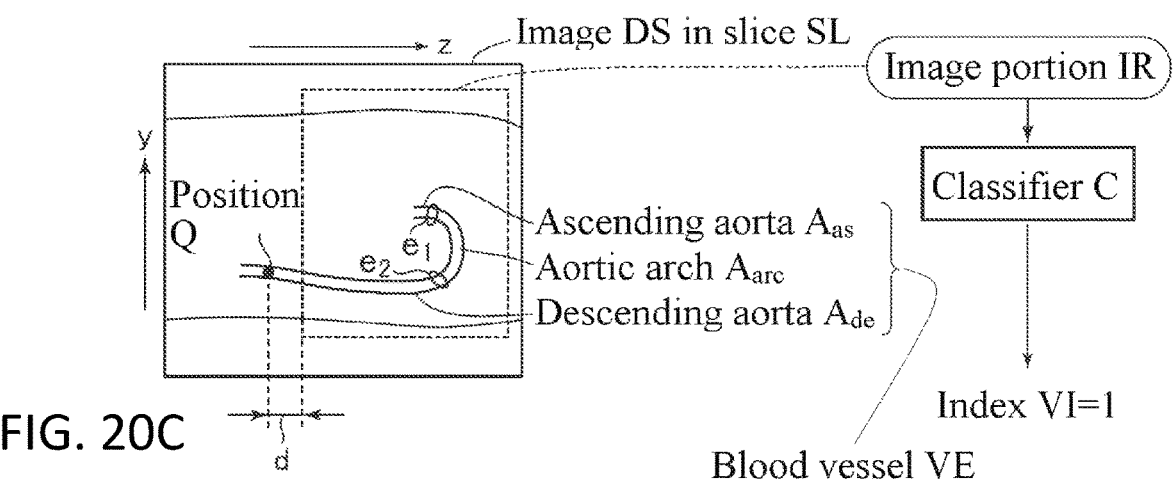

FIGS. 20A-20C are explanatory diagrams showing different perspectives when $\theta_i=\theta_k$. The image portion IR extracted from the slice SL at $\theta_k$ contains all of the ascending aorta $A_{as}$, aortic arch $A_{arc}$, and descending aorta $A_{de}$. In this case, the classifier C outputs one as the value of the index VI, so that the determining unit 111 determines that the angle at which the slice SL contains the blood vessel VE to be detected is $\theta_i=\theta_k$.

Thus, a plane at $\theta_i=\theta_k$ may be obtained as the oblique plane OB (see FIGS. 10A, 10B, 10C) longitudinally cutting the blood vessel VE. The blood vessel VE is thus detected. After detecting the blood vessel VE, the flow goes to step ST9.

Figure 21:
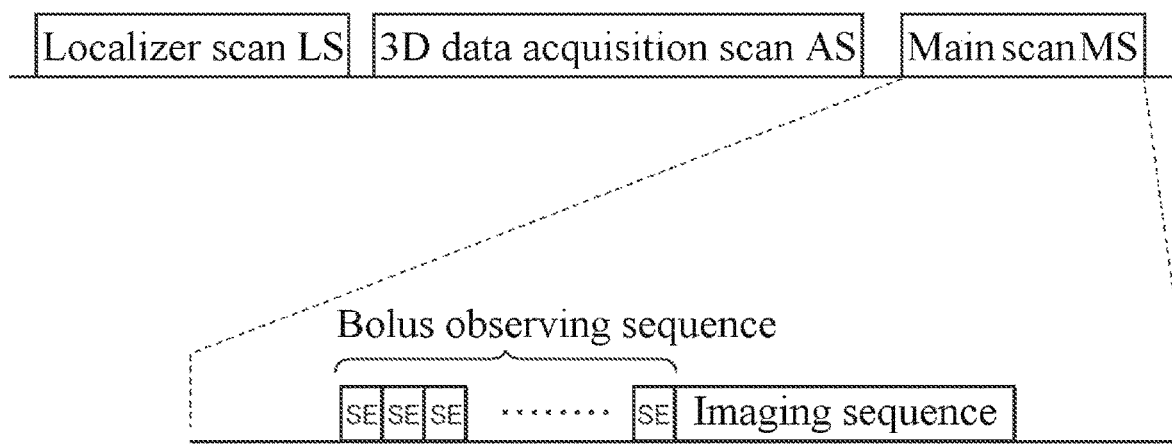
FIG. 21 is an explanatory diagram for the main scan MS.
Figure 22:
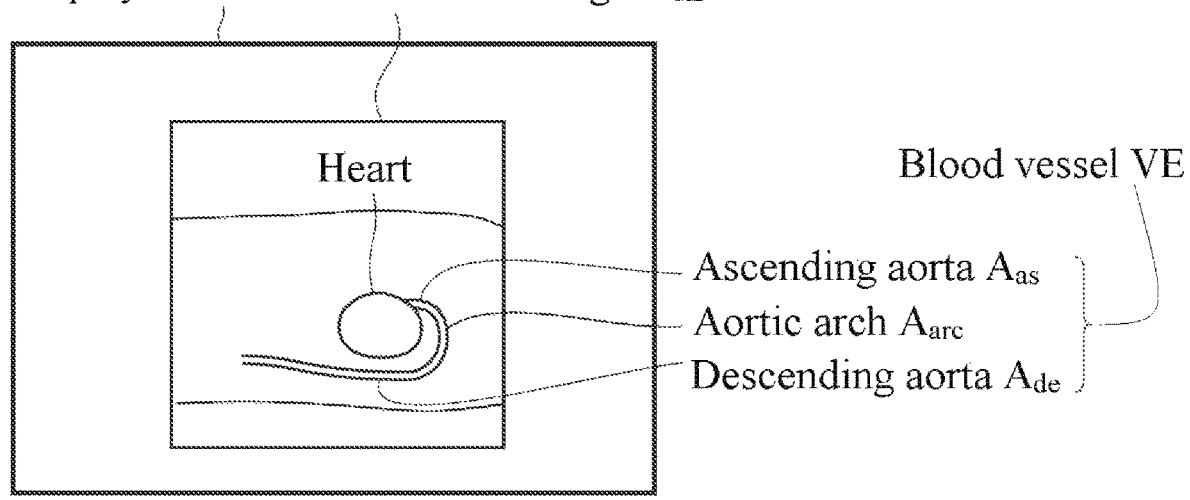
FIG. 22 is a diagram schematically showing a differential image $D_{dif}$ displayed in a display section.

At step ST9, a main scan MS is performed. FIG. 21 is an explanatory diagram for the main scan MS. In the main scan MS, a sequence SE for acquiring a cross-sectional image in the oblique plane OB at $\theta_k$ is repetitively performed. Each time the sequence SE is performed, the image producing unit 101 produces a cross-sectional image in the oblique plane OB at $\theta_k$. The image producing unit 101 then produces a differential image $D_{dif}$ between the latest cross-sectional image and an immediately preceding cross-sectional image. The differential image $D_{dif}$ is displayed in the display section. FIG. 22 schematically shows the differential image $D_{dif}$ displayed in the display section.

Each time the sequence SE is performed, the differential image $D_{dif}$ is updated almost in real time. Therefore, an imaging technologist can visually recognize the latest differential image by viewing the display section.

Moreover, in the main scan MS, a contrast medium is injected into the subject 14 before or during performance of the sequence SE.

The operator confirms whether or not a bolus of the contrast medium has entered the blood vessel VE from the heart while viewing the differential image $D_{dif}$ displayed in the display section. Since the differential image $D_{dif}$ is an image derived by differentiating between the latest cross-sectional image and immediately preceding cross-sectional image, the cross-sectional image displayed in the display section is generally a dark image before the bolus of the contrast medium enters the blood vessel VE. However, once the bolus of the contrast medium has entered the blood vessel VE, a portion of the differential image $D_{dif}$ corresponding to the bolus of the contrast medium becomes brighter. The imaging technologist can thus visually recognize that the bolus of the contrast medium has entered the blood vessel VE. When the imaging technologist has recognized that the contrast medium has entered the blood vessel VE, he/she operates the operating section to input a command for starting an imaging sequence for acquiring an image of the liver. Upon inputting of the command, the bolus observing sequence SE is terminated and execution of the imaging sequence is started.

Once data required for producing an image of the liver has been collected, the main scan MS is terminated. The flow is thus completed.

According to the present embodiment, the position Q of the cross section of the descending aorta $A_{de}$ is detected from within the 3D image DT of the subject 14 (see FIG. 13). With reference to the detected position Q of the cross section of the descending aorta $A_{de}$, the angle $\theta_i$ of the slice SL is changed within a specific angular range $\theta_1 \leq \theta_i \leq \theta_n$, and it is decided whether or not the blood vessel VE is contained in the slice SL for each angle $\theta_i$ (see FIGS. 15A, 15B, 15C to 20A, 20B, 20C). The angle $\theta_k$ of the slice SL (see FIGS. 20A, 20B, 20C) at which the blood vessel VE to be detected is contained in the slice SL can thus be obtained, so that the blood vessel VE may be detected by using the technique in the present embodiment even for a blood vessel that is difficult to detect using the method involving defining a plurality of axial planes.

According to the present embodiment, a cross-sectional image in the oblique plane OB longitudinally cutting the blood vessel VE is produced almost in real time by performing the bolus observing sequence SE, and a differential image $D_{dif}$ between the latest cross-sectional image and immediately preceding cross-sectional image is displayed in the display section (see FIG. 22). The imaging technologist can thus visually recognize the time at which the bolus of the contrast medium has entered the blood vessel VE by viewing the displayed screen, so that an imaging scan can be performed at a desired time.

According to the present embodiment, the slice SL is defined with the position Q of the cross section of the descending aorta $A_{de}$ serving as a reference position (see FIGS. 15A, 15B, 15C to 20A, 20B, 20C). However, the slice SL may be defined with reference to a position different from the position Q.

According to the present embodiment, the angle $\theta_i$ of the slice SL intersecting the 3D image is changed within a specific angular range $\theta_1 \leq \theta_i \leq \theta_n$. (see FIGS. 15A, 15B, 15C to 20A, 20B, 20C). The angular range $\theta_1 \leq \theta_i \leq \theta_n$ is defined taking account of the standard shape of the blood vessel VE, the standard size of the blood vessel VE, the standard position of the blood vessel VE relative to the heart, etc. Therefore, an angular range in which the blood vessel VE to be detected is unlikely to lie within the 3D image is excluded from the angular range $\theta_1 \leq \theta_i \leq \theta_n$ in which the angle of the slice SL is to be changed. The angle of the slice SL may thus be changed within the angular range $\theta_1 \leq \theta_i \leq \theta_n$ in which the blood vessel VE is possibly likely to lie, so that the computation time required to identify the value of the angle $\theta_i$ may be reduced.

According to the present embodiment, the classifier C created using a machine learning technique is used to decide whether or not the blood vessel VE is contained in the slice SL. However, a technique different from machine learning may be used to decide whether or not the blood vessel VE is contained in the slice SL.

According to the present embodiment, a range of the image portion IR is determined based on the position Q of the cross section of the descending aorta $A_{de}$ near the edge of the liver (see FIGS. 17A, 17B, 17C). However, the range of the image portion IR may be determined based on a position farther away from the liver or the heart than the position Q is.

According to the present embodiment, the slice SL is rotated around the axis α of rotation passing through the position Q of the cross section of the descending aorta $A_{de}$ in parallel with the z-direction (see FIGS. 15A, 15B, 15C to 20A, 20B, 20C). However, the slice SL may be rotated around an axis of rotation offset from the position Q or an axis of rotation oblique to the z-direction insofar as the blood vessel VE may be detected.

According to the present embodiment, the image portion IR is extracted from the image DS in the slice SL, and the classifier C executes classification processing within the extracted image portion IR (see FIGS. 18A, 18B, 18C). However, the classification processing may be executed in the whole region of the image DS in the slice SL without extracting the image portion IR from the image DS in the slice SL.

According to the present embodiment, the 3D data acquisition scan AS (see FIG. 3) is performed. However, a 2D scan may be performed in place of the 3D scan insofar as the blood vessel VE to be detected may be detected.

Moreover, according to the present embodiment, the localizer scan LS is performed on a body part including the liver (see FIG. 6). However, the scan range for the localizer scan LS may be extended to include the blood vessel VE to be detected (the ascending aorta $A_{as}$, aortic arch $A_{arc}$, and descending aorta $A_{de}$) in the scan range for the localizer scan LS and an image of the portion of the blood vessel VE obtained by the localizer scan LS may be employed in place of the 3D image DT (FIG. 8). In this case, the 3D data acquisition scan AS is unnecessary, so that the total time required for imaging on the subject 14 may be reduced.

According to the present embodiment, the oblique plane OB (see FIGS. 10A, 10B, 10C) is obtained by defining one slice SL with reference to the position Q of the 3D image DT, and finding an angle $\theta_i = \theta_k$ at which the slice SL contains the blood vessel VE to be detected. However, the oblique plane OB may be obtained by defining a plurality of slices SL1 to SLz arranged in parallel with one another at the position Q of the 3D image DT and in the vicinity of the position Q, finding an angle $\theta_i = \theta_{k1}$ to $\theta_{kz}$ at which each slice contains the blood vessel VE to be detected, and obtaining the oblique plane OB based on $\theta_{k1}$ to $\theta_{kz}$. In this case, for example, an average of $\theta_{k1}$ to $\theta_{kz}$ may be set to the angle $\theta_k$ of the oblique plane OB. Since the angle $\theta_k$ of the oblique plane OB may be determined to further reduce the positional offset between the blood vessel VE and oblique plane OB by using the plurality of slices SL1 to SLz, it is possible to improve accuracy in detecting the blood vessel VE. When the plurality of slices SL1 to SLz are defined, the thickness of each slice may be set to be smaller than the diameter of the blood vessel VE. Moreover, it is possible to define the plurality of slices SL1 to SLz to cross one another.

The present embodiment describes a case in which the blood vessel VE including the ascending aorta $A_{as}$, aortic arch $A_{arc}$, and descending aortic arch $A_{de}$ are detected. However, the present invention is not limited to detection of the blood vessel VE, and may be applied to any blood vessel that is difficult to detect by the technique involving defining a plurality of axial planes. For example, the carotid in the neck is a blood vessel having a plurality of branching portions from the neck toward the head, so that it is difficult to detect the vessel by the method involving defining a plurality of axial planes. However, according to the present invention, an angle $\theta_i$ of the slice SL at which the plurality of branching portions in the carotid are contained in the slice SL may be identified by changing the angle of the slice SL. Therefore, the present invention may be applied to cases in which blood vessels of various shapes in the human body is detected. Moreover, the object to be detected in the present invention is not limited to an artery, and the present invention may be applied to cases in which a vein is detected.

I claim:

1. A blood vessel detection apparatus comprising:
an image producing unit for producing an image of a first body part containing a blood vessel;
a defining unit for defining a slice intersecting said image based on a reference position within said first body part, said slice being defined so that an angle of said slice is changeable with respect to said blood vessel;
a unit for obtaining an index, said unit executing classification processing for classifying said blood vessel within said slice for each said angle and obtaining an index representing a result of the classification; and
a determining unit for determining an angle at which said slice contains said blood vessel based on said index.

2. The blood vessel detection apparatus as recited in claim 1, wherein said defining unit changes said slice within a range from a first angle to a second angle.

3. The blood vessel detection apparatus as recited in claim 2, wherein said unit for obtaining an index obtains said index using a classifier for classifying a blood vessel from an image in said slice.

4. The blood vessel detection apparatus as recited in claim 3, wherein said unit for obtaining an index extracts an image portion used for obtaining said index from within the image in said slice, and said classifier executes classification processing for classifying a blood vessel from within said image portion.

5. The blood vessel detection apparatus as recited in claim 4, wherein said unit for obtaining an index determines a range of said image portion based on said reference position.

6. The blood vessel detection apparatus as recited in claim 1, wherein said defining unit rotates said slice around an axis passing through said reference position.

7. The blood vessel detection apparatus as recited in claim 1, further comprising:
selecting unit for selecting a first cross-sectional image from among a plurality of cross-sectional images each containing a cross section of said blood vessel;
cross-section detecting unit for detecting the cross section of said blood vessel from within said first cross-sectional image; and
locating unit for locating a position of a cross section corresponding to the cross section of said blood vessel detected by said cross-section detecting unit from within the image of said first body part;
wherein said defining unit uses the position of the cross section located by said locating unit as said reference position.

8. The blood vessel detection apparatus as recited in claim 7, wherein each of said plurality of cross-sectional images is a cross-sectional image in an axial plane.

9. The blood vessel detection apparatus as recited in claim 7, wherein said blood vessel includes an ascending aorta, an aortic arch, and a descending aorta, and the cross section detected by said locating unit is a cross section of the descending aorta.

10. The blood vessel detection apparatus as recited in claim 1, wherein the image of said first body part is an image obtained by a 3D scan.

11. A magnetic resonance imaging apparatus comprising:
an image producing unit for producing an image of a first body part containing a blood vessel;
a defining unit for defining a slice intersecting said image based on a reference position within said first body part, said slice being defined so that an angle of said slice is changeable with respect to said blood vessel;
a unit for obtaining an index, said unit executing classification processing for classifying said blood vessel within said slice for each said angle and obtaining an index representing a result of the classification; and
a determining unit for determining an angle at which said slice contains said blood vessel based on said index.

12. A program for causing a computer to execute:
image producing processing of producing an image of a first body part containing a blood vessel;
defining processing of defining a slice intersecting said image based on a reference position within said first body part, said slice being defined so that an angle of said slice is changeable with respect to said blood vessel;
processing of obtaining an index, said processing executing classification processing for classifying said blood vessel within said slice and obtaining an index representing a result of the classification for each said angle; and
determining processing of determining an angle at which said slice contains said blood vessel based on said index.

* * * * *